US008263775B2

(12) United States Patent
Chai et al.

(10) Patent No.: US 8,263,775 B2
(45) Date of Patent: Sep. 11, 2012

(54) INSULIN-REGULATED AMINOPEPTIDASE (IRAP) INHIBITORS AND USES THEREOF

(75) Inventors: Siew Yeen Chai, Burwood East (AU); Michael William Parker, Newport (AU); Anthony Lloyd Albiston, Brunswick East (AU); Frederick A. O. Mendelsohn, Carlton (AU); Keith Geoffrey Watson, Surrey Hills (AU)

(73) Assignees: Howard Florey Institute, Parkville (AU); St. Vincent's Institute of Medical Research, Fitzroy (AU)

( * ) Notice: Subject to any disclaimer, the term of this patent is extended or adjusted under 35 U.S.C. 154(b) by 0 days.

(21) Appl. No.: 12/743,225

(22) PCT Filed: Nov. 18, 2008

(86) PCT No.: PCT/AU2008/001715
§ 371 (c)(1),
(2), (4) Date: Sep. 29, 2010

(87) PCT Pub. No.: WO2009/065169
PCT Pub. Date: May 28, 2009

(65) Prior Publication Data
US 2011/0021563 A1    Jan. 27, 2011

Related U.S. Application Data

(60) Provisional application No. 60/989,037, filed on Nov. 19, 2007.

(51) Int. Cl.
*C07D 407/04*    (2006.01)
(52) U.S. Cl. .................. 546/167; 546/282.7
(58) Field of Classification Search .............. None
See application file for complete search history.

(56) References Cited

U.S. PATENT DOCUMENTS

| 5,281,619 | A  | 1/1994 | Dell et al. ............ 514/454 |
| 6,680,332 | B1 | 1/2004 | Konkoy et al. |
| 2003/0065018 | A1 | 4/2003 | Cai et al. |
| 2003/0114418 | A1 | 6/2003 | Pulaski et al. |
| 2004/0097581 | A1 | 5/2004 | Konkoy et al. |

FOREIGN PATENT DOCUMENTS

| EP | 0 537 949 | | 4/1993 |
| EP | 0 599 514 | | 6/1994 |
| EP | 1 241 256 | | 9/2002 |
| WO | WO 0134591 | A1 * | 5/2001 |
| WO | 02/092594 | | 11/2002 |
| WO | 03/011304 | | 2/2003 |
| WO | 2006/026832 | | 3/2006 |

OTHER PUBLICATIONS

Vippagunta et al., Crystalline solids, 48 Adv. Drug Delivery Rev. 3-26 (2001).*

F. Zaragoza Dorwald, Side Reactions in Organic Synthesis; A Guide to Successful Synthesis Design, Wiley-VCH, Weinheim, Preface, p. IX (2005).*
Extended European Search Report, mailed Jul. 29, 2010, for European Application No. 05778990.1, 9 pages.
International Search Report, mailed Feb. 3, 2009, for PCT/AU2008/001715, 3 pages.
STN File Registry, CAS Registration No. 451519-48-5, Entered Sep. 16, 2002.
STN File Registry, CAS Registration No. 451519-36-1, Entered Sep. 16, 2002.
STN File Registry, CAS Registration No. 451518-34-6, Entered Sep. 16, 2002.
STN File Registry, CAS Registration No. 451517-89-8, Entered Sep. 16, 2002.
STN File Registry, CAS Registration No. 452362-55-9, Entered Sep. 18, 2002.
Written Opinion of the International Searching Authority, mailed Feb. 3, 2009, for PCT/AU2008/001715, 6 pages.
International Preliminary Report on Patentability, for International Application No. PCT/AU2005/001380, dated Mar. 13, 2007, 4 pages.
LookChem, "4H-Naphtho[1,2-b]pyran-3-carbonitrile, 2-amino-4-(2,4-dichlorophenyl)-," Downloaded Sep. 15, 2011, Retrieved from <URL:http://www.lookchem.com/cas-346/346436-68-8.html>, 1 page.
The Merck Index, "1,2-Benzopyran," provided by Knovel (Merck Sharp & Dohme Corp.), 2006 and 2011, 1 page.
Written Opinion of the International Searching Authority, for International Application No. PCT/AU2005/001380, mailed Nov. 18, 2005, 3 pages.
Brühlmann et al., "Coumarins Derivatives as Dual Inhibitors of Acetylcholinesterase and Monoamine Oxidase," *J. Med. Chem.* 44:3195-3198, 2001.
Evers et al., "Principles of the pharmacotherapy of dementia," in Charney et al (ed.), *Neurobiology of Mental Illness*, 2nd ed., Oxford University Press, 2004, pp. 863-872, 13 pages.
Rigg, "Pharmacologic Management of Behavior and Cognitive Impairment in Adults with Brain Injury," in Cristian (ed.), *Medical Management of Adults with Neurologic Disabilities*, Demos Medical Publishing, 2009, pp. 251-264, 18 pages.
Ettmayer et al., "Lessons Learned from Marketed and Investigational Prodrugs," *J. Med. Chem.* 47(10):2393-2404, May 6, 2004.
McGaugh et al., "Drug enhancement of memory consolidation: historical perspective and neurobiological implications," *Psychopharmacology* 202:3-14, 2009.
Testa, "Prodrug research: futile of fertile?," *Biochemical Pharmacology* 68:2097-2106, 2004.
Tozer et al., *Introduction to Pharmacokinetics and Pharmacodynamics: The Quantitative Basis of Drug Therapy*, Lippincott Williams & Wilkins, 2006, Chapter 11, "Variability," pp. 219-247, 34 pages.
Wermuth, "Similarity in drugs: reflections on analogue design," *Drug Discovery Today* 11(7/8):348-354, Apr. 2006.
Wright et al., "Brain renin-angiotensin—A new look at an old system," *Progress in Neurobiology* 95:49-67, 2011.

* cited by examiner

*Primary Examiner* — Janet Andres
*Assistant Examiner* — Timothy R Rozof
(74) *Attorney, Agent, or Firm* — Seed IP Law Group PLLC

(57) ABSTRACT

The present invention relates to inhibitors of insulin-regulated aminopeptidase (IRAP) and methods for inhibiting same, as well as compositions comprising said inhibitors. In particular, the inhibitors of the present invention may be useful in therapeutic applications including enhancing memory and learning functions.

5 Claims, No Drawings

INSULIN-REGULATED AMINOPEPTIDASE (IRAP) INHIBITORS AND USES THEREOF

FIELD OF THE INVENTION

The present invention relates to novel compounds for use as inhibitors of insulin-regulated aminopeptidase (IRAP) and methods for inhibiting same, as well as compositions comprising said compounds. In particular, the compounds of the present invention may be useful in therapeutic applications including enhancing memory and learning functions.

DESCRIPTION OF THE PRIOR ART

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Insulin-regulated aminopeptidase (MAP) is a 165 kDa glycoprotein that is widely distributed in many tissues including fat, muscles, kidney, adrenal, lung and heart (Keller et al., 1995; Rogi et al., 1996; Zhang et al., 1999). In the brain, it occurs as a smaller 140 kDa protein, probably due to differential glycosylation (Keller et al., 1995; Zhang et al., 1999). It is a type II integral membrane protein belonging to the M1 family of zinc-dependent metallopeptidases and possesses a large C-terminal extracellular tail which contains the catalytic site, a single transmembrane domain and a smaller N-terminal intracellular domain (Keller et al., 1995; Rogi et al., 1996). Initially cloned from a rat epididymal fat pad cDNA library as a marker protein (vp165) for a specialised vesicle containing the insulin-responsive glucose transporter GLUT4 (Keller et al., 1995), the same protein was cloned concurrently from human placental cDNA library as oxytocinase (Rogi et al., 1996), an enzyme which was thought to have an important role in degrading oxytocin. The $AT_4$ receptor has also recently been identified as the transmembrane enzyme insulin regulated aminopeptidase (IRAP) via mass spectral analysis of tryptic peptides generated from $AT_4$ receptor protein purified from bovine adrenal membranes (Albiston et al., 2001). Analysis of the biochemical and pharmacological properties of IRAP confirm that it is, in fact, the $AT_4$ receptor (Albiston et al., 2001). Although isolated by three independent groups from different tissue sources and thought to subserve distinct physiological roles, properties and characteristics of this protein remain consistent.

The $AT_4$ ligands, angiotensin IV (Ang IV), its analogues Nle-Ang IV and Norleucinal Ang IV, and the structurally distinct peptide LVV-hemorphin 7 (LVV-H7), all bind with high affinity and relative specificity to a pharmacologically distinct binding site, termed the $AT_4$ receptor. All the $AT_4$ ligands, Ang IV, Nle-Ang IV, and LVV-H7, were demonstrated in vitro to be inhibitors of the aminopeptidase activity of IRAP as assessed by cleavage of the synthetic substrate Leu-β-naphthylamide (Albiston et al., 2001; Lew et al., 2003). Both Ang IV and LVV-H7 display competitive kinetics indicating that $AT_4$ ligands mediate their effects by binding to the catalytic site of IRAP. Using the same system it has also been demonstrated that although the peptides Ang IV and LVV-H7 bind to the catalytic site they are not cleaved by IRAP (Lew et al., 2003).

Central administration of the peptide $AT_4$ ligands, Mg IV, its more stable analogues, or LVV-H7, in normal animals has been shown to lead to improved performance of memory tasks in both passive avoidance and spatial learning paradigms. The initial effects were observed in the passive avoidance paradigm in rats where an intracerebro-ventricular dose (1 nmol) of Ang IV increased the latency in re-entering the dark chamber after an aversive stimulus (Braszko et al., 1988; Wright et al., 1993; Wright et al., 1996). Chronic infusion (6 days) of an Ang IV analogue into the lateral ventricle of rats at a dose of between 0.1 and 0.5 nmol/h enhanced performance in the swim maze, a spatial memory paradigm. In the Barnes maze, another spatial learning task, treatment of rats with 100 pmoles or 1 nmol of the peptide $AT_4$ ligands, $Nle^1$-Ang IV or LVV-H7, decreased the time taken to achieve learner criteria in this paradigm (Lee et al., 2004). Control animals treated with artificial cerebrospinal fluid took 7 days to achieve learner criteria, whereas animals treated with $Nle^1$-Ang IV or LVV-H7, at a concentration of either 100 pmoles or 1 nmole, achieved learner criteria in 3-4 days (Lee et al., 2004). This observation strongly indicates that the two peptides tested not only improved memory, but also enhanced spatial learning.

Not only did peptide $AT_4$ ligands enhance memory and learning in normal animals, the peptides reversed memory deficits induced (1) chemically by a muscarinic antagonist or (2) mechanically by knife-cut lesion of the perforant pathway. A more stable analogue of Ang IV, Nle-Ang IV, given acutely into the lateral ventricles, reversed the memory deficits induced by the muscarinic receptor antagonist, scopolamine, in a spatial learning paradigm (Pederson et al., 1998; Pederson et al., 2001). In the swim maze paradigm, memory deficits induced by bilateral perforant pathway lesion can be reversed by an acute dose (1 nmol) of another Ang IV analogue, Norleucinal Ang IV (Wright et al., 1999). The other $AT_4$ ligand, LVV-H7, given acutely prior to the conditioning trial in the passive avoidance paradigm, has also been found to reverse the memory deficit induced by scopolamine (Albiston et al., 2004).

The mechanisms for IRAP inhibitors facilitating memory are not fully understood, but recent studies implicate neuroendocrine mechanisms of action. Inhibition of IRAP may extend the half-life of neuropeptides that modify learning and memory processes (Albiston, 2003). A number of IRAP peptide substrates including arginine-vasopressin, oxytocin, met-enkephalin, somatostatin, dynorphin and lys-bradykinin have previously been associated with memory (Herbst, 1997; Lew, 2003). Moreover, studies have shown that peptidergic neurotransmission is altered in neurodegenerative diseases leading to memory loss. IRAP is found in high concentrations in brain regions involved in processing cognitive function including the cerebral cortex, hippocampus, basal forebrain and amygdale (Fernando, 2005) where it is co-expressed in neurons with the glucose transporter, GLUT4. It has recently been demonstrated that IRAP inhibitors increase activity-evoked glucose uptake into the pyramidal neurons of the hippocampus (J neurochem submitted). Glucose is a potent modulator of learning and memory in both humans and rodents with increases in glucose demand in the hippocampus occurring during memory processing (McNay, 2000; Dash, 2006). Therefore, one potential mechanism by which compounds may facilitate memory is through the potentiation of glucose uptake into neurons.

IRAP therefore provides a target for the development of agents which may enhance or improve memory and learning. Accordingly, inhibitors of IRAP, which may disrupt or interfere with IRAP functional activity may have useful therapeutic and/or prophylactic applications in the treatment of cognitive and memory disorders or in enhancing memory and learning.

WO 2006/026832 discloses a class of benzo-fused compounds for use as IRAP inhibitors. Nevertheless, there remains the need for identification of compounds which may be useful in the treatment or prevention of memory disorders or improve memory or learning.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The singular forms "a", "an" and "the" include plural aspects unless the context clearly dictates otherwise.

It has now been found that certain benzo-fused compounds within the scope of the disclosure of WO 2006/026832 have a surprisingly improved IRAP inhibitory activity when compared to the most active compound exemplified therein.

Accordingly, in a first aspect, the present invention provides a compound of Formula (I)

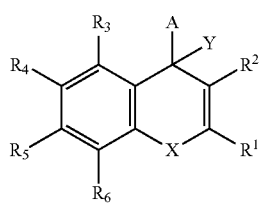

wherein A is aryl, heteroaryl carbocyclyl or heterocyclyl, each of which may be optionally substituted, when $R^1$ is $NHCOR_8$; or quinolinyl, isoquinolinyl, cinnolinyl, quinazolinyl, quinoxalinyl, 1,8-naphthyridyl, phthalazinyl or pteridinyl, each of which may be optionally substituted, when $R^1$ is $NR^7R^8$, $NHCOR_8$, $N(COR_8)_2$, $N(COR_7)(COR_8)$, $N=CHOR_8$ or $N=CHR_8$;

X is O, NR' or S, wherein R' is hydrogen, optionally substituted alkyl, optionally substituted alkenyl, optionally substituted alkynyl, optionally substituted aryl, optionally substituted acyl, optionally substituted heteroaryl, optionally substituted carbocyclyl or optionally substituted heterocyclyl;

$R^7$ and $R^8$ are independently selected from hydrogen, optionally substituted alkyl, optionally substituted aryl, or $R^7$ and $R^8$, together with the nitrogen atom to which they are attached form a 3-8-membered ring which may be optionally substituted;

$R^2$ is CN, $CO_2R^9$, $C(O)O(O)R^9$, $C(O)R^9$ or $C(O)NR^9R^{10}$ wherein $R^9$ and $R^{10}$ are independently selected from alkyl, alkenyl, alkynyl, aryl, heteroaryl, carbocyclyl, heterocyclyl, each of which may be optionally substituted, and hydrogen; or $R^9$ and $R^{10}$, together with the nitrogen atom to which they are attached, form a 3-8-membered ring which may be optionally substituted;

$R^3$-$R^6$ are independently selected from hydrogen, halo, nitro, cyano alkyl, alkenyl, alkynyl, aryl, heteroaryl, heterocyclyl, carbocyclyl, hydroxy, alkoxy, alkenyloxy, alkynyloxy, alkynyloxy, aryloxy, heteroaryloxy, heterocyclyloxy, amino, acyl, acyloxy, carboxy, carboxyester, methylenedioxy, amido, thio, alkylthio, alkenylthio, alkynylthio, arylthio, heteroarylthio, heterocyclylthio, carbocyclylthio, acylthio and azido, each of which may be optionally substituted where appropriate, or any two adjacent $R^3$-$R^6$, together with the atoms to which they are attached, form a 3-8-membered ring which may be optionally substituted; and Y is hydrogen or $C_{1-10}$alkyl, or a pharmaceutically acceptable salt or solvate thereof.

In another aspect, the present invention provides a method for inhibiting IRAP activity which comprises contacting IRAP with an inhibitory amount of a compound of formula (I), or a pharmaceutically acceptable salt or solvate thereof. Inhibition of IRAP activity can be performed in vitro or in vivo, such as in vivo in a subject. The invention therefore also provides a method for inhibiting IRAP activity in a subject in need thereof, which comprises administering to said subject an inhibitory effective amount of a compound of formula (I), or a pharmaceutically acceptable salt or solvate thereof.

Compounds described herein may be useful in treating a disease or condition in which excessive or undesirable IRAP activity plays a role. Thus, the invention further provides a method for treating a disease or condition in which IRAP activity is implicated, in a subject in need thereof, comprising the step of administering to said subject an effective amount of a compound of formula (I), or a pharmaceutically acceptable salt or solvate thereof. The invention also provides for the use of a compound of formula (I), or a pharmaceutically acceptable salt or solvate thereof in the manufacture of a medicament for treating a disease or condition in which IRAP activity is implicated, as well as for the use of a compound of formula (I), or a pharmaceutically acceptable salt or solvate thereof, for treating a disease or condition in which IRAP activity is implicated. In one embodiment, the disease is Alzheimer's disease.

As described above, IRAP inhibitors have been shown to improve memory and enhance spatial learning as well as reversing memory deficits.

Accordingly, in another aspect, the present invention provides a method for enhancing memory and/or learning in a subject, comprising the step of administering to said subject a compound of formula (I) or a pharmaceutically acceptable salt or solvate thereof. The invention thus also provides for the use of a compound of formula (I), or a pharmaceutically acceptable salt or solvate thereof in the manufacture of a medicament for enhancing memory and/or learning in a subject, as well as for the use of a compound of formula (I), or a pharmaceutically acceptable salt or solvate thereof, for enhancing memory and/or learning in a subject.

The invention also provides agents and compositions comprising a compound according to Formula (I) or a pharmaceutically acceptable salt or solvate thereof together with a pharmaceutically acceptable carrier or excipient.

DESCRIPTION OF THE INVENTION

As used herein, the term "alkyl" or "alk", used either alone or in compound words denotes straight chain, or branched alkyl, preferably $C_{1-20}$ alkyl, e.g. $C_{1-10}$ or $C_{1-6}$. Examples of straight chain and branched alkyl include methyl, ethyl, n-propyl, isopropyl, n-butyl, sec-butyl, t-butyl, n-pentyl, 1,2-dimethylpropyl, 1,1-dimethyl-propyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2,-trimethylpropyl, 1,1,2-trimethylpropyl, heptyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethyl-pentyl, 1,2,3-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyl-octyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propyloctyl, 1-, 2- or 3-butyl-heptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2-pentylheptyl and the like. Where an alkyl group is referred to generally as "propyl", butyl" etc, it will be understood that this can refer to any of straight or branched isomers where appropriate. An alkyl group may be optionally substituted by one or more optional substituents as herein defined.

The term "alkenyl" as used herein denotes groups formed from straight chain or branched hydrocarbon residues containing at least one carbon to carbon double bond including ethylenically mono-, di- or poly-unsaturated alkyl groups as previously defined, preferably $C_{2-20}$ alkenyl (e.g. $C_{2-10}$ or $C_{2-6}$). Examples of alkenyl include vinyl, allyl, 1-methylvinyl, butenyl, iso-butenyl, 3-methyl-2-butenyl, 1-pentenyl, 1-hexenyl, 3-hexenyl, 1-heptenyl, 3-heptenyl, 1-octenyl, 1-nonenyl, 2-nonenyl, 3-nonenyl, 1-decenyl, 3-decenyl, 1,3-butadienyl, 1-4,pentadienyl, 1,3-hexadienyl and 1,4-hexadienyl. An alkenyl group may be optionally substituted by one or more optional substituents as herein defined.

As used herein the term "alkynyl" denotes groups formed from straight chain or branched hydrocarbon residues containing at least one carbon-carbon triple bond including ethynically mono-, di- or poly-unsaturated alkyl groups as previously defined. Unless the number of carbon atoms is specified the term preferably refers to $C_{2-20}$ alkynyl (e.g. $C_{2-10}$ or $C_{2-6}$). Examples include ethynyl, 1-propynyl, 2-propynyl, and butynyl isomers, and pentynyl isomers. An alkynyl group may be optionally substituted by one or more optional substituents as herein defined.

Terms written as "[group]oxy" refer to a particular group when linked by oxygen, for example, the terms "alkoxy", "alkenoxy", "alkynoxy" and "aryloxy" and "acyloxy" respectively denote alkyl, alkenyl, alkynyl, aryl and acyl groups as hereinbefore defined when linked by an oxygen atom. Terms written as "[group]thio" refer to a particular group when linked by sulfur, for example, the terms "alkylthio", "alkenylthio", alkynylthio" and "arylthio" respectively denote alkyl, alkenyl, alkynyl, aryl groups as hereinbefore defined when linked by a sulfur atom. Similarly, a term written as "[groupA]groupB" is intended to refer to a groupA when linked by a divalent form of groupB, for example, "hydroxyalkyl" is a hydroxy group when linked by an alkylene group.

The term "halogen." ("halo") denotes fluorine, chlorine, bromine or iodine (fluoro, chloro, bromo or iodo).

The term "aryl" (or "carboaryl)", or the abbreviated form "ar" used in compound words such as "aralkyl", denotes any of mono-, bi- or polcyclic, (including conjugated and fused) hydrocarbon ring systems containing an aromatic residue. Examples of aryl include phenyl, biphenyl, terphenyl, quaterphenyl, naphthyl, tetrahydronaphthyl (tetralinyl), anthracenyl, dihydroanthracenyl, benzanthracenyl, dibenzanthracenyl, phenanthrenyl, fluorenyl, pyrenyl, idenyl, isoindenyl, indanyl, azulenyl and chrysenyl. Particular examples of aryl include phenyl and naphthyl. An aryl group may be optionally substituted by one or more optional substituents as herein defined.

The term "carbocyclyl" includes any of non-aromatic monocyclic, bicyclic and polycyclic, (including fused, bridged or conjugated) hydrocarbon residues, e.g. $C_{3-20}$ (such as $C_{3-10}$ or $C_{3-8}$). The rings may be saturated, for example cycloalkyl, or may possess one or more double bonds (cycloalkenyl) and/or one or more triple bonds (cycloalkynyl). Examples of particular carbocyclyl are monocyclic 5-6-membered or bicyclic 9-10 membered ring systems. Suitable examples include cyclopropyl, cyclobutyl, cyclopentyl, cyclohexyl, cycloheptyl, cyclooctyl, cyclononyl, cyclodecyl, cyclopentenyl, cyclohexenyl, cyclooctenyl, cyclopentadienyl, cyclohexadienyl, cyclooctatetraenyl and decalinyl. A carbocyclyl group may be optionally substituted by one or more optional substituents as herein defined. In particular, a monocarbocyclyl group may be substituted by a bridging group to form a bicyclic bridged group.

The term "heterocyclyl" when used alone or in compound words includes any of monocyclic, bicyclic or polycyclic, (including fuse, bridged or conjugated) hydrocarbon residues, such as $C_{3-20}$ (e.g. $C_{3-10}$ or $C_{3-8}$) wherein one or more carbon atoms are independently replaced by a heteroatom so as to provide a group containing a non-aromatic heteroatom containing ring. Suitable heteroatoms include, O, N, S, P and Se, particularly O, N and S. Where two or more carbon atoms are replaced, this may be by two or more of the same heteroatom or by different heteroatoms. The heterocyclyl group may be saturated or partially unsaturated, e.g. possess one or more double bonds. Particularly preferred heterocyclyl are monocyclic 5-6- and bicyclic 9-10-membered heterocyclyl. Suitable examples of heterocyclyl groups may include azridinyl, oxiranyl, thiiranyl, azetidinyl, oxetanyl, thietanyl, 2H-pyrrolyl, pyrrolidinyl, 1-, 2- and 3-pyrrolinyl, piperidyl, piperazinyl, morpholinyl, indolinyl, imidazolidinyl, imidazolinyl, pyrazolidinyl, thiomorpholinyl, dioxanyl, tetrahydrofuranyl, tetrahydropyranyl, tetrahydropyrrolyl, tetrahydrothiophenyl (tetramethylene sulfide), pyrazolinyl, dioxalanyl, thiazolidinyl, isoxazolidinyl, dihydropyranyl, oxazinyl, thiazinyl, thiomorpholinyl, oxathianyl, dithianyl, trioxanyl, thiadiazinyl, dithiazinyl, trithianyl, azepinyl, oxepinyl, thiepinyl, indenyl, indanyl, 3H-indolyl, isoindolinyl, 4H-quinolazinyl, chromenyl, chromanyl, isochromanyl, benzoxazinyl (2H-1,3, 2H-1, 4-, 1H-2,3-, 4H-3,1-4H-1,4) pyranyl and dihydropyranyl. A heterocyclyl group may be optionally substituted by one or more optional substituents as defined herein.

The term "heteroaryl" includes any of monocyclic, bicyclic, polycyclic, (fused or conjugated) hydrocarbon residues, wherein one or more carbon atoms are replaced by a heteroatom so as to provide a residue having at least one aromatic heteroatom-containing ring. Exemplary heteroaryl have 3-20 ring atoms, e.g. 3-10. Particularly preferred heteroaryl are 5-6 monocyclic and 9-10 membered bicyclic ring systems. Suitable heteroatoms include, O, N, S, P and Se, particularly O, N and S. Where two or more carbon atoms are replaced, this may be by two or more of the same heteroatom or by different heteroatoms. Suitable examples of heteroaryl groups may include pyridyl, pyrrolyl, thienyl, imidazolyl, furanyl, benzothienyl, isobenzothienyl, benzofuranyl, isobenzofuranyl, indolyl, isoindolyl, pyrazolyl, pyrazinyl, pyrimidinyl, pyridazinyl, indolizinyl, quinolyl, isoquinolyl, phthalazinyl, 1,5-naphthyridinyl, quinozalinyl, quinazolinyl, quinolinyl, oxazolyl, thiazolyl, isothiazolyl, isoxazolyl, triazolyl, oxadialzolyl, oxatriazolyl, triazinyl, tetrazolyl and furazanyl. A heteroaryl group may be optionally substituted by one or more optional substituents as defined herein.

The term "acyl" either alone or in compound words denotes a group containing the moiety C=O (and not being a carboxylic acid, ester or amide) Preferred acyl includes C(O)—R, wherein R is hydrogen or an alkyl, alkenyl, alkynyl, aryl, heteroaryl, carbocyclyl, or heterocyclyl residue.

Examples of acyl include formyl, straight chain or branched alkanoyl (e.g. $C_{1-20}$) such as, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl; cycloalkylcarbonyl such as cyclopropylcarbonyl cyclobutylcarbonyl, cyclopentylcarbonyl and cyclohexylcarbonyl; aroyl such as benzoyl, toluoyl and naphthoyl; aralkanoyl such as phenylalkanoyl (e.g. phenylacetyl, phenylpropanoyl, phenylbutanoyl, phenylisobutylyl, phenylpentanoyl and phenylhexanoyl) and naphthylalkanoyl (e.g. naphthylacetyl, naphthylpropanoyl and naphthylbutanoyl]; aralkenoyl such as phenylalkenoyl (e.g. phenylpropenoyl, phenylbutenoyl, phenylmethacryloyl, phenylpentenoyl and phenylhexenoyl and naphthylalkenoyl (e.g. naphthylpropenoyl, naphthylbutenoyl and naphthylpentenoyl); aryloxyalkanoyl such as phenoxyacetyl and phenoxypropionyl; arylthiocarbamoyl such as phenylthiocarbamoyl; arylglyoxyloyl such as phenylglyoxyloyl and naphthylglyoxyloyl; arylsulfonyl such as phenylsulfonyl and napthylsulfonyl; heterocycliccarbonyl; heterocyclicalkanoyl such as thienylacetyl, thienylpropanoyl, thienylbutanoyl, thienylpentanoyl, thienylhexanoyl, thiazolylacetyl, thiadiazolylacetyl and tetrazolylacetyl; heterocyclicalkenoyl such as heterocyclicpropenoyl, heterocyclicbutenoyl, heterocyclicpentenoyl and heterocyclichexenoyl; and heterocyclicglyoxyloyl such as thiazolyglyoxyloyl and thienylglyoxyloyl. The R residue may be optionally substituted as described herein.

In this specification "optionally substituted" is taken to mean that a group may be unsubstituted or further substituted or fused (so as to form a condensed bi- or polycyclic group) with one, two, three or more of organic and inorganic groups, including those selected from: alkyl, alkenyl, alkynyl, carbocyclyl, aryl, heterocyclyl, heteroaryl, acyl, aralkyl, alkylaryl, alkylheterocyclyl, alkylheteroaryl, alkylcarbocyclyl, halo, haloalkyl, haloalkenyl, haloalkynyl, haloaryl, halocarbocyclyl, haloheterocyclyl, haloheteroaryl, haloacyl, haloaryalkyl, hydroxy, hydroxyalkyl, hydroxyalkenyl, hydroxyalkynyl, hydroxycarbocyclyl, hydroxyaryl, hydroxyheterocyclyl, hydroxyheteroaryl, hydroxyacyl, hydroxyaralkyl, alkoxyalkyl, alkoxyalkenyl, alkoxyalkynyl, alkoxycarbocyclyl, alkoxyaryl, alkoxyheterocyclyl, alkoxyheteroaryl, alkoxyacyl, alkoxyaralkyl, alkoxy, alkenyloxy, alkynyloxy, aryloxy, carbocyclyloxy, aralkyloxy, heteroaryloxy, heterocyclyloxy, acyloxy, haloalkoxy, haloalkenyloxy, haloalkynyloxy, haloaryloxy, halocarbocyclyloxy, haloaralkyloxy, haloheteroaryloxy, haloheterocyclyloxy, haloacyloxy, nitro, nitroalkyl, nitroalkenyl, nitroalkynyl, nitroaryl, nitroheterocyclyl, nitroheteroaryl, nitrocarbocyclyl, nitroacyl, nitroaralkyl, amino ($NH_2$), alkylamino, dialkylamino, alkenylamino, alkynylamino, arylamino, diarylamino, aralkylamino, diaralkylamino, acylamino, diacylamino, heterocyclamino, heteroarylamino, carboxy, carboxyester, amido, alkylsulphonyloxy, arylsulphenyloxy, alkylsulphenyl, arylsulphenyl, thio, alkylthio, alkenylthio, alkynylthio, arylthio, aralkylthio, carbocyclylthio, heterocyclylthio, heteroarylthio, acylthio, sulfoxide, sulfonyl, sulfonamido, aminoalkyl, aminoalkenyl, aminoalkynyl, aminocarbocyclyl, aminoaryl, aminoheterocyclyl, aminoheteroaryl, aminoacyl, aminoaralkyl, thioalkyl, thioalkenyl, thioalkynyl, thiocarbocyclyl, thioaryl, thioheterocyclyl, thioheteroaryl, thioacyl, thioaralkyl, carboxyalkyl, carboxyalkenyl, carboxyalkynyl, carboxycarbocyclyl, carboxyaryl, carboxyheterocyclyl, carboxyheteroaryl, carboxyacyl, carboxyaralkyl, carboxyesteralkyl, carboxyesteralkenyl, carboxyesteralkynyl, carboxyestercarbocyclyl, carboxyesteraryl, carboxyesterheterocyclyl, carboxyesterheteroaryl, carboxyesteracyl, carboxyesteraralkyl, amidoalkyl, amidoalkenyl, amidoalkynyl, amidocarbocyclyl, amidoaryl, amidoheterocyclyl, amidoheteroaryl, amidoacyl, amidoaralkyl, formylalkyl, formylalkenyl, formylalkynyl, formylcarbocyclyl, formylaryl, formylheterocyclyl, formylheteroaryl, formylacyl, formylaralkyl, acylalkyl, acylalkenyl, acylalkynyl, acylcarbocyclyl, acylaryl, acylheterocyclyl, acylheteroaryl, acylacyl, acylaralkyl, sulfoxidealkyl, sulfoxidealkenyl, sulfoxidealkynyl, sulfoxidecarbocyclyl, sulfoxidearyl, sulfoxideheterocyclyl, sulfoxideheteroaryl, sulfoxideacyl, sulfoxidearalkyl, sulfonylalkyl, sulfonylalkenyl, sulfonylalkynyl, sulfonylcarbocyclyl, sulfonylaryl, sulfonylheterocyclyl, sulfonylheteroaryl, sulfonylacyl, sulfonylaralkyl, sulfonamidoalkyl, sulfonamidoalkenyl, sulfonamidoalkynyl, sulfonamidocarbocyclyl, sulfonamidoaryl, sulfonamidoheterocyclyl, sulfonamidoheteroaryl, sulfonamidoacyl, sulfonamidoaralkyl, nitroalkyl, nitroalkenyl, nitroalkynyl, nitrocarbocyclyl, nitroaryl, nitroheterocyclyl, nitroheteroaryl, nitroacyl, nitroaralkyl, cyano, sulfate, sulfonate, phosphonate and phosphate groups. Optional substitution may also be taken to refer to where a $CH_2$ group in a chain or ring is replaced by a carbonyl group (C=O) or a thiocarbonyl group (C=S), where 2 adjacent or non-adjacent carbon atoms (e.g. 1,2- or 1,3) are substituted by one end each of a —O—$(CH_2)_s$—O— or —$NR^x$—$(CH_2)_s$—$NR^x$— group, wherein s is 1 or 2 and each $R^x$ is independently H or $C_{1-6}$alkyl, and where 2 adjacent or non-adjacent atoms, independently selected from C and N, are substituted by one end each of a $C_{1-5}$alkylene or $C_{2-5}$alkenylene group (so as to form a bridged group).

Exemplary optional substituents include those selected from: alkyl, (e.g. $C_{1-6}$alkyl such as methyl, ethyl, propyl, butyl), cycloalkyl (e.g. $C_{3-6}$cycloalkyl, such as cyclopropyl, cyclobutyl, cyclopentyl or cyclohexyl), hydroxyalkyl (e.g. hydroxy$C_{1-6}$alkyl, such as hydroxymethyl, hydroxyethyl, hydroxypropyl), alkoxyalkyl (e.g. $C_{1-6}$alkoxy$C_{1-6}$alkyl, such as methoxymethyl, methoxyethyl, methoxypropyl, ethoxymethyl, ethoxyethyl, ethoxypropyl), alkoxy (e.g. $C_{1-6}$alkoxy, such as methoxy, ethoxy, propoxy, butoxy), alkoxyalkoxy (e.g. $C_{1-6}$alkoxy$C_{1-6}$ alkoxy, such as methoxymethoxy, methoxyethoxy, methoxypropoxy, ethoxymethoxy, ethoxyethoxy, ethoxypropoxy, propoxymethoxy, propoxyethoxy, propoxypropoxy) cycloalkoxy (e.g. cyclopropoxy, cyclobutoxy, cyclopentoxyl, cyclohexyloxy), halo, haloalkyl(e.g. halo$C_{1-6}$alkyl, such as chloromethyl, difluoromethyl, trifluoromethyl, trichloromethyl, tribromomethyl), haloalkoxy (e.g. halo$C_{1-6}$alkoxy), hydroxy, thio (—SH), sulfonyl, sulfonamido, phenyl (which itself may be further substituted e.g., by one or more $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, OC(O)$C_{1-6}$alkyl, $NH_2$, NH$C_{1-6}$alkyl, NHC(O)$C_{1-6}$alkyl and N$C_{1-6}$alkyl$C_{1-6}$alkyl), benzyl (wherein benzyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, OC(O)$C_{1-6}$alkyl, $NH_2$, NH$C_{1-6}$alkyl, NHC(O)$C_{1-6}$alkyl and N$C_{1-6}$alkyl$C_{1-6}$alkyl), phenoxy (wherein phenyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, OC(O)$C_{1-6}$alkyl, $NH_2$, NH$C_{1-6}$alkyl, NHC(O)$C_{1-6}$alkyl and N$C_{1-6}$alkyl$C_{1-6}$alkyl), benzyloxy (wherein benzyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, haloC$_{1-6}$alkyl, haloC$_{1-6}$alkoxy, cyano, nitro, OC(O)C$_{1-6}$alkyl, NH$_2$, NHC$_{1-6}$alkyl, NHC(O)C$_{1-6}$alkyl and NC$_{1-6}$alkylC$_{1-6}$alkyl), NH$_2$, alkylamino (e.g. —NHC$_{1-6}$alkyl, such as methylamino, ethylamino, propylamino etc), dialkylamino (e.g. —NH(C$_{1-6}$alkyl)$_2$, such as dimethylamino, diethylamino, dipropylamino), acylamino (e.g. —NHC(O)C$_{1-6}$alkyl, such as —NHC(O)CH$_3$), phenylamino (i.e. —NHphenyl, wherein phenyl itself may be further substituted e.g., by one or more of C$_{1-6}$alkyl, halo, hydroxy, hydroxyC$_{1-6}$alkyl, hydroxyC$_{1-6}$alkoxy C$_{1-6}$alkoxy, C$_{1-6}$alkoxyC$_{1-6}$alkyl, C$_{1-6}$alkoxyC$_{1-6}$alkoxy, haloC$_{1-6}$alkyl, haloC$_{1-6}$alkoxy, cyano, nitro, OC(O)C$_{1-6}$alkyl, NH$_2$, NHC$_{1-6}$ alkyl, NHC(O)C$_{1-6}$alkyl and NC$_{1-6}$alkylC$_{1-6}$alkyl), nitro, cyano, formyl, —C(O)-alkyl (e.g. —C(O)C$_{1-6}$alkyl, such as acetyl), O—C(O)-alkyl (e.g. —OC(O)C$_{1-6}$alkyl, such as acetyloxy), benzoyl (wherein benzyl itself may be further substituted e.g., by one or more of C$_{1-6}$alkyl, halo, hydroxy, hydroxyC$_{1-6}$alkyl, C$_{1-6}$alkoxy, C$_{1-6}$alkoxyC$_{1-6}$alkyl, C$_{1-6}$alkoxyC$_{1-6}$alkoxy, haloC$_{1-6}$alkyl, haloC$_{1-6}$alkoxy, cyano, nitro, OC(O)C$_{1-6}$alkyl, NH$_2$, NHC$_{1-6}$alkyl, NHC(O)C$_{1-6}$alkyl and NC$_{1-6}$alkylC$_{1-6}$alkyl), benzoyloxy (wherein benzyl itself may be further substituted e.g., by one or more of C$_{1-6}$alkyl, halo, hydroxy, hydroxyC$_{1-6}$alkyl, C$_{1-6}$alkoxy, C$_{1-6}$alkoxyC$_{1-6}$alkyl, C$_{1-6}$alkoxyC$_{1-6}$alkoxy, haloC$_{1-6}$alkyl, haloC$_{1-6}$alkoxy, cyano, nitro, OC(O)C$_{1-6}$alkyl, NH$_2$, NHC$_{1-6}$alkyl, NHC(O)C$_{1-6}$alkyl and NC$_{1-6}$alkylC$_{1-6}$alkyl), CO$_2$H, CO$_2$alkyl (e.g. CO$_2$C$_{1-6}$alkyl such as methyl ester, ethyl ester, propyl ester, butyl ester), CO$_2$phenyl (wherein phenyl itself may be further substituted e.g., by one or more of C$_{1-6}$alkyl, halo, hydroxy, hydroxyC$_{1-6}$alkyl, C$_{1-6}$alkoxy, C$_{1-6}$alkoxyC$_{1-6}$alkyl, C$_{1-6}$alkoxyC$_{1-6}$alkoxy, haloC$_{1-6}$alkyl, haloC$_{1-6}$alkoxy, cyano, nitro, OC(O)C$_{1-6}$alkyl, NH$_2$, NHC$_{1-6}$alkyl, NHC(O)C$_{1-6}$alkyl and NC$_{1-6}$alkylC$_{1-6}$alkyl), CO$_2$benzyl (wherein benzyl itself may be further substituted e.g., by one or more of C$_{1-6}$alkyl, halo, hydroxy, hydroxyC$_{1-6}$alkyl, C$_{1-6}$alkoxy, C$_{1-6}$alkoxyC$_{1-6}$alkyl, C$_{1-6}$alkoxyC$_{1-6}$alkoxy, haloC$_{1-6}$alkyl, haloC$_{1-6}$alkoxy, cyano, nitro, OC(O)C$_{1-6}$alkyl, NH$_2$, NHC$_{1-6}$alkyl, NHC(O)C$_{1-6}$alkyl and NC$_{1-6}$alkylC$_{1-6}$alkyl), CONH$_2$, C(O)NHphenyl (wherein phenyl itself may be further substituted e.g., by one or more of C$_{1-6}$alkyl, halo, hydroxy, hydroxyC$_{1-6}$alkyl, C$_{1-6}$alkoxy, C$_{1-6}$alkoxyC$_{1-6}$ alkyl, C$_{1-6}$alkoxyC$_{1-6}$alkoxy, haloC$_{1-6}$alkyl, haloC$_{1-6}$ alkoxy, cyano, nitro, OC(O)C$_{1-6}$alkyl, NH$_2$, NHC$_{1-6}$alkyl, NHC(O)C$_{1-6}$alkyl and NC$_{1-6}$alkylC$_{1-6}$alkyl), C(O)NHbenzyl (wherein benzyl itself may be further substituted e.g., by one or more of C$_{1-6}$alkyl, halo, hydroxy, hydroxyC$_{1-6}$alkyl, C$_{1-6}$alkoxy, C$_{1-6}$alkoxyC$_{1-6}$alkyl, C$_{1-6}$alkoxyC$_{1-6}$alkoxy, haloC$_{1-6}$alkyl, haloC$_{1-6}$alkoxy, cyano, nitro, OC(O)C$_{1-6}$alkyl, NH$_2$, NHC$_{1-6}$alkyl, NHC(O)C$_{1-6}$alkyl and NC$_{1-6}$alkylC$_{1-6}$alkyl), C(O)NHalkyl (e.g. C(O)NHC$_{1-6}$ alkyl such as methyl amide, ethyl amide, propyl amide, butyl amide) C(O)Ndialkyl (e.g. C(O)N(C$_{1-6}$alkyl)$_2$) aminoalkyl (e.g., HNC$_{1-6}$alkyl-, C$_{1-6}$alkylHN—C$_{1-6}$alkyl- and (C$_{1-6}$alkyl)$_2$N—C$_{1-6}$alkyl-), thioalkyl (e.g., HSC$_{1-6}$alkyl-), carboxyalkyl (e.g., HO$_2$CC$_{1-6}$alkyl-), carboxyesteralkyl (e.g., C$_{1-6}$alkylO$_2$CC$_{1-6}$alkyl-), amidoalkyl (e.g., H$_2$N(O)CC$_{1-6}$alkyl-, H(C$_{1-6}$alkyl)N(O)CC$_{1-6}$alkyl-), formylalkyl (e.g., OHCC$_{1-6}$alkyl-), acylalkyl (e.g., C$_{1-6}$alkyl(O)CC$_{1-6}$alkyl-), nitroalkyl (e.g., O$_2$NC$_{1-6}$alkyl-), replacement of CH$_2$ with C=O, replacement of CH$_2$ with C=S, substitution of 2 adjacent or non-adjacent carbon atoms (e.g. 1,2 or 1,3) by one end each of a —O—(CH$_2$)$_s$—O— or —NR'—(CH$_2$)$_s$—NR'— group, wherein s is 1 or 2 and each R' is independently H or C$_{1-6}$alkyl, and substitution of 2 adjacent or non-adjacent atoms, independently selected from C and N, by a C$_{2-5}$alkylene or C$_{2-5}$alkenylene group.

The term "sulfoxide", either alone or in a compound word, refers to a group —S(O)R wherein R is selected from hydrogen, alkyl, alkenyl, alkynyl, aryl, heteroaryl, heterocyclyl, carbocyclyl, and aralkyl. Examples of R include hydrogen, C$_{1-20}$alkyl, phenyl and benzyl.

The term "sulfonyl", either alone or in a compound word, refers to a group S(O)$_2$—R, wherein R is selected from hydrogen, alkyl, alkenyl, alkynyl, aryl, heteroaryl, heterocyclyl, carbocyclyl, acyl, and aralkyl. Examples of R include hydrogen, C$_{1-20}$alkyl, phenyl and benzyl.

The term "sulfonamide", or "sulfonamyl" of "sulfonamido", either alone or in a compound word, refers to a group S(O)$_2$NRR wherein each R is independently selected from hydrogen, alkyl, alkenyl, alkynyl, aryl, heteroaryl, heterocyclyl, carbocyclyl, acyl, and aralkyl. Examples of R include hydrogen, C$_{1-20}$alkyl, phenyl and benzyl. In an embodiment at least one R is hydrogen. In another form, both R are hydrogen.

A "sulfate" group refers to a group —OS(O)$_2$OR wherein each R is independently selected from hydrogen, alkyl, alkenyl, alkynyl, aryl, heteroaryl, heterocyclyl, carbocyclyl, acyl, and aralkyl. Examples of R include hydrogen, C$_{1-20}$alkyl, phenyl and benzyl.

The term "sulfonate" refers to a group SO$_3$R wherein each R is independently selected from hydrogen, alkyl, alkenyl, alkynyl, aryl, heteroaryl, heterocyclyl, carbocyclyl, acyl, and aralkyl. Examples of R include hydrogen, C$_{1-20}$alkyl, phenyl and benzyl.

The term "thio" is intended to include groups of the formula "—SR" wherein R can be hydrogen (thiol), alkyl, alkenyl, alkynyl, aryl, carbocyclyl, heteroaryl, heterocyclyl, aralkyl, and acyl. Examples of R include hydrogen, C$_{1-20}$alkyl, phenyl and benzyl.

The term, "amino" is used here in its broadest sense as understood in the art and includes groups of the formula —NR$^A$R$^B$ wherein R$^A$ and R$^B$ may be any independently selected from hydrogen, hydroxy alkyl, alkoxyalkyl, alkenyl, alkynyl, aryl, carbocyclyl, heteroaryl, heterocyclyl, aralkyl, and acyl, each of which may be optionally substituted. R$^A$ and R$^B$, together with the nitrogen to which they are attached, may also form a monocyclic, or polycyclic ring system e.g. a 3-10 membered ring, particularly, 5-6 and 9-10 membered systems. Examples of "amino" include —NH$_2$, —NHalkyl (e.g. —NHC$_{1-20}$alkyl), —NHalkoxyalkyl, —NHaryl (e.g. —NHphenyl), —NHaralkyl (e.g. —NHbenzyl), —NHacyl (e.g. —NHC(O)C$_{1-20}$alkyl, —NHC(O)phenyl), —Ndialkyl (wherein each alkyl, for example C$_{1-20}$, may be the same or different) and 5 or 6 membered rings, optionally containing one or more same or different heteroatoms (e.g. O, N and S). Reference to groups written as "[group]amino" is intended to reflect the nature of the R$^A$ and R$^B$ groups. For example, "alkylamino" refers to —NR$^A$R$^B$ where one of R$^A$ or R$^B$ is alkyl. "Dialkylamino" refers to —NR$^A$R$^B$ where R$^A$ and R$^B$ are each (independently) an alkyl group.

The term "amido" is used here in its broadest sense as understood in the art and includes groups having the formula C(O)NR$^A$R$^B$, wherein R$^A$ and R$^B$ are as defined as above. Examples of amido include C(O)NH$_2$, C(O)NHalkyl (e.g. C$_{1-20}$alkyl), C(O)NHaryl (e.g. C(O)NHphenyl), C(O)NHaralkyl (e.g. C(O)NHbenzyl), C(O)NHacyl (e.g. C(O)NHC(O)C$_{1-20}$alkyl, C(O)NHC(O)phenyl), C(O)Nalkylalkyl (wherein each alkyl, for example C$_{1-20}$, may be the same or different) and 5 or 6 membered rings, optionally containing one or more same or different heteroatoms (e.g. O, N and S).

The term "carboxy ester" is used here in its broadest sense as understood in the art and includes groups having the formula CO$_2$R, wherein R may be selected from groups including alkyl, alkenyl, alkynyl, aryl, carbocyclyl, heteroaryl, heterocyclyl, aralkyl, and acyl. Particular examples of carboxy ester include $CO_2C_{1-20}$alkyl, $CO_2$aryl (e.g. $CO_2$phenyl), $CO_2$aralkyl (e.g. $CO_2$ benzyl).

In some embodiments, when $R^1$ is $NHCOR_8$, A is selected from optionally substituted 5-6-membered aryl, heteroaryl, carbocyclyl and heterocyclyl, e.g. phenyl, pyridyl (attached at C2, C3 or C4), pyrazinyl, pyrimidinyl (attached at C2, C4 or C5), pyridazinyl (attached at C3 or C4), s-triazinyl (attached at C2, C4 or C6), as-triazinyl (attached at C3, C5 or C6), v-triazinyl (attached at C4, C5 or C6), furanyl (attached at C2 or C3), pyrrolyl (attached at C2 or C3), thienyl (attached at C2 or C3), cyclopentyl, cyclohexyl, cyclopentadienyl, cyclohexadienyl, pyranyl, piperidinyl, piperazinyl, morpholinyl, pyrolidinyl and pyrrolinyl. In certain embodiments A is optionally substituted 5-6-membered aryl or optionally substituted heteroaryl, particularly optionally substituted phenyl or optionally substituted pyridyl.

In other embodiments, when $R^1$ is $NHCOR_8$, A is selected from optionally substituted naphthyl, an optionally substituted 9-10 membered bicyclic heteroaryl group, including N-containing 10-membered groups.

Some particular examples of $NHCOR_8$ include $NHCOC_{1-6}$alkyl (e.g. NHCOMe, NHCOEt, NHCOPr), NHCOphenyl and NHCObenzyl. In further examples, where $R^1$ is $NHCOC_{1-6}$alkyl, it is NHCOMe. In other examples it is $NHCOC_{2-6}$alkyl (e.g. NHCOEt, NHCOPr or NHCOBu).

In other embodiments, when $R^1$ is $NR^7R^8$, $NHCOR_8$, $N(COR_8)_2$, $N(COR_7)(COR_8)$, $N=CHOR_8$ or $N=CHR_8$, A is a bicyclic N-containing heteroaryl group such as quinolinyl, isoquinolinyl, cinnolinyl, quinazolinyl, quinoxalinyl, 1,8-naphthyridyl, phthalazinyl or pteridinyl, each of which may be substituted or unsubstituted. The group may be attached via any carbon atom of the ring system. In certain embodiments, the group may be attached via the 2-, 3-, 6- or 7-position as appropriate. In other embodiments, the group may be attached via the 1-, 4-, 5- or 8-position as appropriate. Some particular examples contemplated herein are 3- and 4-quinolinyl, particularly 3-quinolinyl. In further embodiments, A is unsubstituted.

In some embodiments, when $R^1$ is $NR^7R^8$, $R^1$ is $NHR^8$, wherein $R^8$ is optionally substituted alkyl or optionally substituted aryl. In other embodiments when $R^1$ is $NR^7R^8$, $R^7$ and $R^8$ together with the N atom to which they are attached, form a 3-8-membered ring, e.g. together are an alkylene group such as $—(CH_2)_q—$ where q is 2, 3, 4 or 5.

In yet further embodiments of the invention, A is a bicyclic N-containing heteroaryl group as described above and $R^1$ is $NHCOR_8$, such as $NHCOC_{1-6}$alkyl. In a particular embodiment, A is 3-quinolinyl and $R^1$ is NHCOMe.

In certain embodiments, when A is quinolinyl, isoquinolinyl, cinnolinyl, quinazolinyl, quinoxalinyl, 1,8-naphthyridyl, phthalazinyl or pteridinyl, particularly quinolinyl, then $R^1$ is $NHR_8$, $N<(CH_2)_q$, $NHCOR_8$, $N(COR_8)_2$, $N(COR_7)(COR_8)$, $N=CHOR_8$ or $N=CHR_8$.

In yet other embodiments of the invention, when A is aryl, carbocyclyl, or heterocyclyl then $R^1$ is $NR^7R^8$, $N(COR_8)_2$, $N(COR_7)(COR_8)$, $N=CHOR_8$ or $N=CHR_8$.

Exemplary optional substituents for A include alkyl, haloalkyl (e.g. mono-, di- or trifluoromethyl, mono-, di-or trichloromethyl and mono-, di-, tri-, tetra, penta- or hexafluoroethyl and mono-, di-, tri-, tetra, penta- or hexachloroethyl), hydroxyalkyl, aminoalkyl, thioalklyl, arylalkyl (e.g. benzyl and phenylethyl), alkoxy, haloalkoxy, hydroxyalkoxyl, aminoalkoxy, alkythio, haloalkythio, hydroxyalkythio, aminoalkylthio, thioalkythio, amino, C(O)alkyl, OC(O)alkyl, aryl (eg. phenyl), carboxy, carboxy ester (e.g. $CO_2$alkyl, $CO_2$aryl), C(O)aryl, OC(O)aryl, nitro, cyano, heteroaryl (e.g. pyridyl), heteroarylalkyl, heterocyclyl, heterocyclylalkyl, hydroxy, thio, methylenedioxy, halo (e.g. Cl, Br) and amido. Where such a substituent is or contains an "alkyl" moiety, it may be $C_{1-10}$alkyl, particularly $C_{1-6}$alkyl, such as methyl, ethyl, i-propyl, n-propyl, n-butyl, sec-butyl or t-butyl.

In one embodiment X is O. In another embodiment X is NR'. In yet another embodiment X is S. In particular examples X is O. Where X is NR', some examples of R' include hydrogen, $C_{1-10}$alkyl, benzyl, phenylethyl, $OC(O)C_{1-10}$alkyl and OC(O)phenyl.

In one embodiment, Y is hydrogen.

Particular examples of $R^7$ and $R^8$ include hydrogen, $C_{1-10}$ alkyl, and phenyl wherein $C_{1-10}$ alkyl and phenyl may be optionally substituted.

Some exemplary substituents for $R^7$ and $R^8$ (including exemplified $R^7$ and $R^8$ as above) include alkyl, haloalkyl (e.g. mono-, di- or trifluoromethyl, mono-, di-or trichloromethyl and mono-, di-, tri-, tetra, penta- or hexafluoroethyl and mono-, di-, tri-, tetra, penta- or hexachloroethyl), hydroxyalkyl, aminoalkyl, thioalkyl, arylalkyl (e.g. benzyl and phenylethyl) alkoxy, haloalkoxy, hydroxyalkoxyl, aminoalkoxy alkythio, haloalkythio, hydroxyalkylthio, aminoalkylthio, thioalkythio, amino, C(O)alkyl OC(O)alkyl, aryl (e.g. phenyl) carboxy, carboxy ester C(O)aryl OC(O)aryl, nitro, cyano, heteroaryl (e.g. pyridyl) heteroarylalkyl, heterocyclyl, heterocyclylalkyl, hydroxy, thio, methylenedioxy, halo (e.g. Cl, Br) and amido or together form a 5-6-membered ring e.g. (piperidyl, morpholinyl). Where such a substituent contains an "alkyl" moiety, preferred alkyl are $C_{1-10}$alkyl, particularly $C_{1-6}$alkyl. Particularly preferred $R^1$ include $NH_2$, $NHC_{1-6}$alkyl, $N(C_{1-6}$alkyl) $(C_{1-6}$alkyl) and $NHC(O)C_{1-6}$alkyl, most preferably $NH_2$.

For $R^2$, examples of $R^9$ and $R^{10}$ include hydrogen, $C_{1-10}$ alkyl, aryl (e.g. phenyl) heteroaryl (e.g. pyridyl). One particularly preferred $R^2$ is cyano (CN). Particular examples of $R^2$ are $CO_2C_{1-10}$ alkyl, (e.g. $CO_2$Me, $CO_2$Et, $CO_2$Pr, $CO_2$Bu etc) and amido, e.g. $CONH_2$.

Examples of suitable $R^3$-$R^6$ include hydrogen, chloro, bromo, $C_{1-10}$ alkyl (including cycloalkyl), $C_{2-10}$ alkenyl (including cycloalkenyl), $C_{2-10}$ alkynyl (including cycloalkynyl), $C_{1-10}$ alkoxy (e.g. methoxy, ethoxy, n- and i-propoxy and n-, sec- and t-butoxy), phenyl, halophenyl, hydroxyphenyl, aminophenyl, alkylphenyl, hydroxy, $NH_2$, $NHC_{1-10}$alkyl, $NC_{1-10}$alkyl$C_{1-10}$alkyl (wherein each alkyl may be the same or different), nitro, haloalkyl, including trifluoromethyl, trichloromethyl, acyl (e.g. $C(O)C_{1-10}$alkyl), acyloxy (e.g. $OC(O)C_{1-10}$alkyl or OC(O)aryl such as OC(O)phenyl), carboxy ester (e.g. $CO_2C_{1-10}$alkyl and $CO_2$ phenyl), $CO_2H$, amido (e.g. $CONHC_{1-10}$alkyl), nitro, cyano, thio, alkylthio (e.g. $SC_{1-10}$alkyl) and 2 of adjacent $R^3$-$R^6$ form methylenedioxy. None, one, two, three or four of $R^3$-$R^6$ may be hydrogen. In one preferred form, 2 or 3 or 4 of $R^3$-$R^6$ are hydrogen. In one particular embodiment, $R^3$, $R^4$ and $R^6$ are all H. In a further embodiment thereof, $R^3$, $R^4$ and $R^6$ are all H and $R^5$ is hydroxy.

Where any two adjacent $R^3$-$R^6$ form a 3-8-membered ring together with the atoms to which they are attached, the ring may be carbocyclic (saturated or partially unsaturated), heterocyclic, aryl or heteroaryl. In some preferred embodiments, the ring formed has 5-6-members. Particularly preferred forms of this embodiment are where $R^5$ and $R^6$ form a ring. Examples of any two adjacent $R^3$-$R^6$ taken together include $—(CH_2)_n—$ where n is 1-7, preferably 1-4, particularly 3 or 4, $—O—CH_2—O—$, $O—(CH_2)_2—O$ $—CH=CH—CH_2=CH—$, $—CH_2—NHCH_2—$, $—(CH_2)_2—NH—CH_2—$, $—CH_2—NH—(CH_2)_2—$, $—(CH_2)_2—NH—$, —NH—(CH$_2$)$_2$—, —NH—CH=CH—, —CH=CH—NH—, —O—CH=CH—, —CH=CH—O—, —S—CH=CH—, —CH=CH—S—, —N=CH—CH=N— O—CH=CH—CH$_2$—, and —CH$_2$—CH=CH—O—. Where appropriate, an N atom within such a ring may be further substituted with alkyl (eg. C$_{1-10}$), aryl (eg. phenyl), arylalkyl (eg. benzyl or phenylethyl), acyl (eg. C(O)C$_{1-10}$alkyl) hydroxyalkyl (eg. C$_{1-10}$), haloalkyl (eg. C$_{1-10}$), carbocyclylalkyl, heteroarylalkyl, heterocyclylalkyl, carbocyclyl, heteroaryl or heterocyclyl.

In yet other embodiments of the invention, X is oxygen, R$^2$ is CO$_2$R$^9$ (such as CO$_2$C$_{1-6}$alkyl, e.g. CO$_2$Me or CO$_2$Et), R$^3$, R$^4$, R$^6$ are all hydrogen, R$^5$ is OH and Y is hydrogen.

Some exemplary compounds contemplated by the invention have the formula:

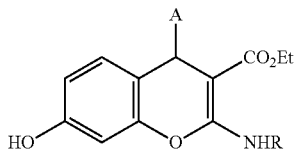

Particular examples thereof are:
(i) A=3-pyridyl, R=C(=O)CH$_3$
(ii) A=3-quinolinyl, R=H
(iii) A=3-quinolinyl, R=C(=O)CH$_3$ Compounds for use in the invention may be prepared via methods known in the art of synthetic organic chemistry, see for example WO 02/092594.

Thus, for the preparation of compounds where X is O, an appropriately substituted phenol compound may be reacted with an appropriate aldehyde and malononitrile in the presence of a base such as piperidine or N,N-diisopropylethylamine in accordance with the generalised Scheme 1 below:

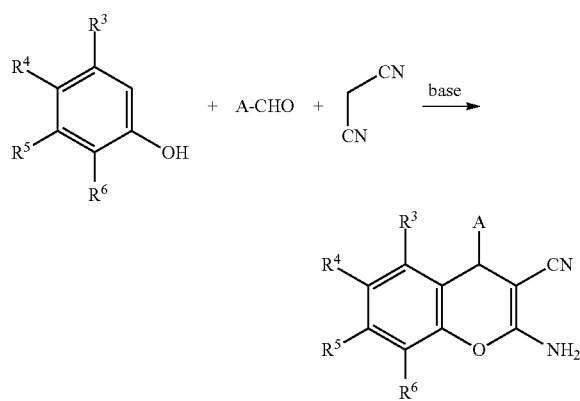

Scheme 1

Alternatively, the aldehyde may be reacted with malononitrile in the presence of a base, and the resulting arylidene intermediate reacted with the appropriate phenol.

In an alternative methodology, the appropriately substituted ortho-aroyl phenol, aniline or benzenethiol can be reacted with malononitrile (or appropriate cyanoacetate, cyanoacetamide or acylacetonitrile) to access the corresponding 4H-chromene, 1,4-dihydroquinoline or 4H-thiochromene as in Scheme 2 below (where P is H or a protecting group as appropriate).

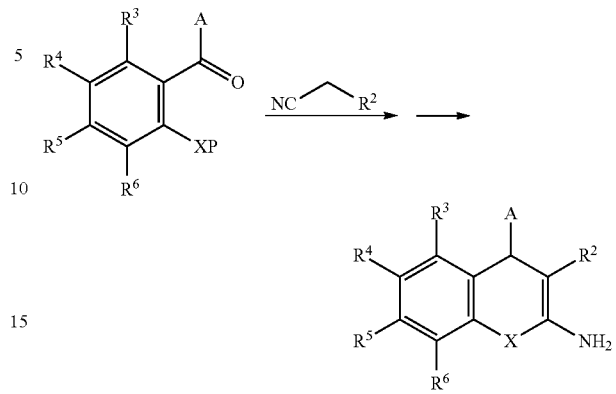

Scheme 2

Suitable dihydroquinoline compounds can also be prepared by reduction of an appropriately substituted or protected quinoline.

Compounds of formula (I), where R$^1$ is other than NH$_2$ may be prepared by converting the amine to the desired group using chemical transformations known in the art, for example as described in *Comprehensive Organic Transformation, A Guide to Functional Group Preparations*, R. C. Larock, VCH, 1989 and *Advanced Organic Chemistry, Reactions, Mechanisms and Structure*, J. March, 3$^{rd}$ Edition, 1985 or 4$^{th}$ Edition, 1992 (the entire contents of which are incorporated herein by reference). Thus, treatment of the amine (NH$_2$) with a suitable acylating agent such as a carboxylic acid, anhydride or chloride in the presence of an appropriate base or catalyst provides access to compounds of formula (I) where R$^1$ is NHCOR$^8$. Alkyl and aryl amines can be prepared by treatment of —NH$_2$ with an appropriate alkyl or aryl halide. Imines may be formed by treating the amine group (NH$_2$) with a suitable carbonyl containing compound such as an aldehyde or ketone in accordance with art known methods.

Similarly, compounds where R$^2$ is other than CN, i.e. carboxylic acid, esters, amides, anhydrides and ketones, may be prepared by transformations known in the art, see in particular Larock, supra, Chapter 9, pp 963-995. Alternatively, reaction of the appropriate phenol, aldehyde and the appropriate cyanoacetate, cyanoacetamide or acylacetonitrile affords access to compounds where R$^2$ is CO$_2$R$^9$, C(O)NR$^9$R$^{10}$, C(O)R$^9$ and C(O)O(O)R$^9$.

Compounds where Y is alkyl can be prepared by treating the benzopyran with DDQ and the subsequent intermediate with CuBr.DMS and an alkyllithium compound.

It will be recognised that during the processes for the preparation of compounds contemplated by the present invention, it may be necessary or desirable to protect certain functional groups which may be reactive or sensitive to the reaction or transformation conditions undertaken (e.g. OH (including diols), NH$_2$, CO$_2$H, SH, C=O). Suitable protecting groups for such functional groups are known in the art and may be used in accordance with standard practice. As used herein, the term "protecting group", refers to an introduced functionality which temporarily renders a particular functional group inactive under certain conditions. Such protecting groups and methods for their installation and subsequent removal at an appropriate stage are described in *Protective Groups in Organic Chemistry*, 3$^{rd}$ Edition, T. W. Greene and P. G. Wutz, John Wiley and Sons, 1999, the entire contents of which are incorporated herein by reference. Exemplary forms of protected groups include:

for amino (NH$_2$)—carbamates (such as Cbz, Boc, Fmoc), benzylamines, acetamides (e.g. acetamide, trifluoroacetamide);

for carbonyl—acetals, ketals, dioxanes, dithianes, and hydrazones;

for hydroxy—ethers (e.g. alkyl ethers, alkoxylalkyl ethers, allyl ethers, silyl ethers, benzyl ethers, tetrahydropyranyl ethers), carboxylic acid esters, acetals (e.g. acetonide and benzylidene acetal);

for thio (SH)—ethers (e.g. alkyl ethers, benzyl ethers), esters for CO$_2$H—esters (e.g. alkyl esters, benzyl esters).

As used herein, the term "inhibit" or variations thereof when used in relation to IRAP activity, such as aminopeptidase activity, includes prevention, interruption, disruption, reduction, retardation or otherwise decrease in the rate or extent of IRAP activity, and thus includes partial inhibition of IRAP activity as well as complete or near complete inhibition.

The level of IRAP inhibitory activity of the compounds disclosed herein can be initially determined in an in vitro assay, which measures the ability of the test compound to inhibit the aminopeptidase activity of IRAP, by assessing the rate or extent of cleavage or degradation of an IRAP aminopeptidase substrate such as Leu-β-naphthylamide or Leu-4-methylcoumaryl-7-amide. Comparison can then be made to a control assay, whereby the rate or extent of cleavage is determined in the absence of the compound. A comparative reduction in the rate or extent of cleavage of the substrate in the presence of the compound can be taken to be a measure of the inhibitory effect of the compound.

Thus, there is also provided a method of determining the IRAP inhibitory activity of a compound, comprising:
(a) incubating IRAP, an IRAP substrate and a compound as described herein; and
(b) assessing the rate or extent of cleavage of the substrate; wherein a reduction or inhibition in the rate or extent of cleavage of the substrate, when compared to a control, is indicative of IRAP inhibitory activity of the compound.

Advantageously, in one or more embodiments of the invention, a compound of Formula (I), or a pharmaceutically acceptable salt or solvate, may exhibit selectivity or specificity for IRAP over other enzymes.

In one or more embodiments, compounds of the invention may potentiate, enhance or otherwise increase glucose uptake into neurons.

Disorders and conditions where undesirable or excessive IRAP aminopeptidase activity is implicated or involved may include memory or learning disorders associated with Alzheimer's disease and other forms of dementia and memory loss (be they age-related, induced through head trauma, hypoxic damage, surgery, cerebral infarcts or chemical means such as neurotoxins). It should also be appreciated that the compounds of the present invention may also be useful in enhancing or improving memory or learning in normal individuals, i.e. those not suffering from cognitive pathologies such as those described above.

Memory or learning (e.g. spatial learning) enhancement refers to an improvement in the ability of a subject to memorize or learn information and can be determined by well established tests. A positive improvement in the "score" or result obtained in such a test compared to a score/result obtained prior to administration of the compounds is taken to be an enhancement in memory or learning as appropriate. In certain embodiments of the invention, the improvement can be expressed as a % (score after administration of compound/score prior to administration of compound) and may represent an improvement of at least about 10%, 20%, 25%, 40%, 50%, 60%, 70%, 80%, 90%, 100%, 150% or 200%.

A number of well known and established tests exist for laboratory animals and rats and mice can be tested using these, which include the Barnes Maze paradigm (Greferath et al., 2000), Barnes Circular Maze test (Lee et al., 2004) or modifications thereof, the Y maze test, or passive avoidance test. Suitable examples of these are briefly outlined below.

1. Barnes Maze

Normal male Sprague-Dawley rats are implanted with cannulas in the lateral ventricles and allowed to recover for at least three days. For the Barnes Circular Maze test, the maze comprises a raised rotatable white circular platform of diameter 1.2 m, with 18 evenly spaced holes in the periphery (diameter 0.09 m). An escape tunnel comprising a black box of internal diameter of 0.16 m width, 0.29 m length and 0.09 m depth is positioned immediately beneath a peripheral hole. Visual cues are placed at various positions around the maze.

For each trial, the animal is placed on the maze platform under the starting chamber, which is a cylindrical chamber located in the centre of the platform, and left for 20 s. Following the twenty seconds disorientation period the chamber is raised. The animals are then allowed 240 s in which to find and utilise the escape tunnel. Each rat receives three consecutive trials per day over ten days. On the first day of the testing period, each rat is placed directly into the escape tunnel for a 2 min familiarisation period. The rat is then replaced into its cage for approximately one minute, after which the animal is injected with either the test compound or artificial cerebrospinal fluid and then replaced into its cage for a further 5 min. Three consecutive trials are then carried out, with a recovery period of 2 min between each trial in its home cage. On subsequent days (days 2 to 8), the familiarisation period prior to the three trials is eliminated from the protocol.

Animals can be administered the compounds of the invention intracerebroventricularly (icv) via a chronic indwelling cannula. These compounds are given 5 mins before the first trial on the first day of testing.

2. Y Maze

The Y-maze test is another behavioural paradigm which measures spatial memory performance, and exploits the natural instinct of rodents to explore novel environments.

The Y maze consists of three identical alleys (30 cm in length, 10 cm in width and 17 cm in height) with the three arms separated by 120° angles. To minimize stress, the maze is located in a sound-attenuated room under dim illumination, with the floor of the maze covered with sawdust. After each trial, the sawdust is mixed to eliminate olfactory cues. For spatial orientation, visual cues are placed on the walls of the testing room.

The test consists of two trials, separated by a time interval known as the intertrial interval. During the acquisition trial, the animals are placed at the distal end of one arm, their heads pointing away from the centre of the maze. The animals are allowed to visit only two accessible arms of the maze for 3 minutes. At the end of the acquisition trial, animals are replaced in their cages for the intertrial interval. During the retention trial, the animals have access to all three arms for 5 minutes. The first arm entered (novel vs familiar), the number of entries and duration of time spent in the novel arm is documented.

A shorter intertrial interval (2 hours) separating the acquisition phase from the retention phase enables amnesiant effects to be detected. Control animals still remember the location of the novel arm and will preferentially spend more time (45-50% of time) in that arm. A longer intertrial interval (e.g. 6 hours) results in the animals not remembering the location of the novel arm and hence spending equal amount of time in all three arms.

Animals are surgically implanted with an infusion cannula in the dorsal third ventricle. Each animal is tested twice, and the intertrial interval of greater than 6 h can be adopted to test for memory-enhancing properties of the test compounds. Animals are administered the compounds intracerebroventricularly via a chronic indwelling cannula. These compounds are given 5 mins before the first acquisition trial. The animals are then returned to their home cages for at least 6 hours and then tested again. The time spent in the novel arm will be a measure of the memory enhancing properties of the test compound.

3. Passive Avoidance

Passive avoidance trials can be used to test the effect of IRAP inhibitors on aversive conditioning behaviour in amnesic animals. The passive avoidance task involves aversive conditioning behaviour to measure facilitation of memory retention and retrieval. The testing can be carried out in an apparatus that consists of a light and a dark compartment separated by a guillotine door. The floor of the dark compartment contains an electrified grid. The passive avoidance task is divided into two trials separated by a 24-48 h inter-trial interval. During the first trial, known as the acquisition trial, the animal is placed in the lit compartment and the guillotine door is closed once the animal enters the dark compartment. Inside the dark chamber, the animal receives a low-level electric shock (0.5 mA for 2 s) via the grid floor. The animal is then returned to its home cage for 24 h or 48 h before being tested. The latency periods to re-enter the dark compartment are taken as a measure of the ability of the animals to remember the aversive stimuli.

Animals are surgically implanted with an infusion cannula in the dorsal third ventricle. Each animal is tested twice, and the intertrial interval of 24 h and 48 h can be adopted to test for memory-enhancing properties of the test compounds. Animals are administered the compounds intracerebroventricularly via a chronic indwelling cannula. These compounds are given 5 mins before the acquisition trial. The animals are then returned to their home cages for 24 h or 48 h and then tested again. The latency in entering the dark chamber will be a measure of the memory-enhancing property of the test compound.

4. Age-Induced Memory Deficit Model

Spatial learning impairment in aged rats is well documented and this deficit can be detected in the Barnes maze paradigm (Greferath et al., 2000). The effect of IRAP inhibitors on aged-induced learning deficits can be tested in the Barnes maze paradigm.

For drug treatment, the animals are implanted with Alzet minipumps (secured subcutaneously in the neck region) which delivers the test compounds chronically into the cerebral ventricles.

5. Animal Model of Alzheimer's Dementia

The effects of the IRAP inhibitors can be tested in a mouse model of Alzheimer's disease, the Tg2576 transgenic mouse (with the Swedish mutation Lys-670-Asn; Met-671-Leu). This mouse model of Alzheimer's disease is commercially available from Taconic Biotechnology, and the mice have demonstrated deficits in spatial learning (water maze) and working memory (spontaneous alternation Y maze).

Memory and learning can be tested in humans by any one of a number of well established neuropsychological tests such as California Verbal Learning Test, Wechsler Memory Scale-III, Hopkins Verbal Learning Test—Revised™, Rey Auditory Verbal Learning Test, and Rey-Osterrieth Complex Figure Design Test.

Subjects to be treated by the compounds and methods of the invention include mammalian subjects: humans, non-primates, livestock animals (including cows, horses, sheep, pigs and goats), companion animals (including dogs, cats, rabbits, guinea pigs), and captive wild animals. Laboratory animals such as rabbits, mice, rats, guinea pigs and hamsters are also contemplated as they may provide a convenient test system. Non-mammalian species such as birds, amphibians and fish may also be contemplated in certain embodiments of the invention. In particular embodiments, the subject is a human subject.

The compounds of the invention are administered to the subject in an IRAP inhibiting, or otherwise treatment effective amount. An IRAP inhibiting amount is an amount which will at least partially interact with IRAP or disrupt IRAP activity. IRAP activity as used herein includes IRAP functional interaction with endogenous ligands, particularly where the functional interaction directly or indirectly promotes memory and/or learning loss. A treatment effective amount is intended to include an amount which, when administered according to the desired dosing regimen, results in a measurable improvement or enhancement in memory or learning, or at least partially attains the desired therapeutic or prophylactic effect of one or more of: alleviating, eliminating or reducing the frequency of one or more of the symptoms of, preventing or delaying the onset of, inhibiting the progression of, or halting or reversing, partially or altogether, the onset or progression of the particular disorder or condition being treated.

Suitable dosage amounts and dosing regimens can be determined by the attending physician and may depend on the particular condition being treated, the severity of the condition as well as the general age, health and weight of the subject.

The active ingredient may be administered in a single dose or a series of doses. While it is possible for the active ingredient to be administered alone, it is preferable to present it as a composition, preferably as a pharmaceutical composition, with one or more pharmaceutically acceptable adjuvants. Thus, the present invention also relates to the use of a compound of formula (I) or a pharmaceutically acceptable salt or solvate thereof in the manufacture of a medicament for inhibiting IRAP activity in a subject.

The formulation of such compositions is well known to those skilled in the art, see for example, *Remington's Pharmaceutical Sciences*, 18$^{th}$ Edition, Mack Publishing, 1990. The composition may contain any suitable carriers, diluents or excipients. These include all conventional solvents, dispersion media, fillers, solid carriers, coatings, antifungal and antibacterial agents, dermal penetration agents, surfactants, isotonic and absorption agents and the like. It will be understood that the compositions of the invention may also include other supplementary physiologically active agents.

The carrier must be pharmaceutically acceptable in the sense of being compatible with the other ingredients of the composition and not injurious to the subject. Compositions include those suitable for oral, rectal, nasal, topical (including dermal, buccal and sublingual), vaginal or parental (including subcutaneous, intramuscular, intravenous, intracerebroventricular and intradermal) administration. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. inert diluent), preservative disintegrant (e.g. sodium starch glycolate, cross-linked polyvinyl pyrrolidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for topical administration in the mouth include lozenges comprising the active ingredient in a flavoured base, usually sucrose and acacia or tragacanth gum; pastilles comprising the active ingredient in an inert basis such as gelatin and glycerin, or sucrose and acacia gum; and mouthwashes comprising the active ingredient in a suitable liquid carrier.

Compositions suitable for topical administration to the skin may comprise the compounds dissolved or suspended in any suitable carrier or base and may be in the form of lotions, gel, creams, pastes, ointments and the like. Suitable carriers include mineral oil, propylene glycol, polyoxyethylene, polyoxypropylene, emulsifying wax, sorbitan monostearate, polysorbate 60, cetyl esters wax, cetearyl alcohol, 2-octyldodecanol, benzyl alcohol and water. Transdermal patches may also be used to administer the compounds of the invention.

Compositions for rectal administration may be presented as a suppository with a suitable base comprising, for example, cocoa butter, glycerin, gelatin or polyethylene glycol.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration (e.g. subcutaneous, intramuscular, intravenous or intracerebroventricular) may include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage compositions are those containing a daily dose or unit, daily sub-dose, as herein above described, or an appropriate fraction thereof, of the active ingredient.

It should be understood that in addition to the active ingredients particularly mentioned above, the compositions of this invention may include other agents conventional in the art having regard to the type of composition in question, for example, those suitable for oral administration may include such further agents as binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

It will be understood that the compounds contemplated herein may be presented as prodrugs of formula (I). Any compound that is a prodrug of a compound of formula (I) is within the scope and spirit of the invention. The term "prodrug" is used in its broadest sense and encompasses those derivatives that are converted in vivo, either enzymatically or hydrolytically, to the compounds of the invention. Such derivatives would readily occur to those skilled in the art, and include, for example, compounds where a free thiol or hydroxy group is converted into an ester, such as an acetate, or thioester or where a free amino group is converted into an amide. Procedures for acylating the compounds of the invention, for example to prepare ester and amide prodrugs, are well known in the art and may include treatment of the compound with an appropriate carboxylic acid, anhydride or chloride in the presence of a suitable catalyst or base. Esters of carboxylic acid (carboxy) groups are also contemplated. Suitable esters $C_{1-6}$alkyl esters; $C_{1-6}$alkoxymethyl esters, for example methoxymethyl or ethoxymethyl; $C_{1-6}$alkanoyloxymethyl esters, for example, pivaloyloxymethyl; phthalidyl esters; $C_{3-8}$cycloalkoxycarbonyl$C_{1-6}$alkyl esters, for example, 1-cyclohexylcarbonyloxyethyl; 1,3-dioxolen-2-onylmethyl esters, for example, 5-methyl-1,3-dioxolen-2-onylmethyl; and $C_{1-6}$alkoxycarbonyloxyethyl esters, for example, 1-methoxycarbonyloxyethyl. Prodrugs of amino functional groups include amides (see, for example, *Adv. BioSci.,* 1979, 20, 369, Kyncl, J. et al), enamines (see, for example, *J. Pharm. Sci.,* 1971, 60, 1810, Caldwell, H. et al), Schiff bases (see, for example, U.S. Pat. No. 2,923,661 and *Antimicrob. Agents Chemother.,* 1981, 19, 1004, Smyth, R. et al), oxazolidines (see, for example, *J. Pharm. Sci,* 1983, 72, 1294, Johansen, M. et al), Mannich bases (see, for example, *J. Pharm. Sci.* 1980, 69, 44, Bundgaard, H. et al and *J. Am. Chem. Soc.,* 1959, 81, 1198, Gottstein, W. et al), hydroxymethyl derivatives (see, for example, *J. Pharm. Sci,* 1981, 70, 855, Bansal, P. et al) and N-(acyloxy)alkyl derivatives and carbamates (see, for example, *J. Med. Chem.,* 1980, 23, 469, Bodor, N. et al, *J. Med. Chem.,* 1984, 27, 1037, Firestone, R. et al, *J. Med. Chem.,* 1967, 10, 960, Kreiger, M. et al, U.S. Pat. No. 5,684,018 and *J. Med. Chem.,* 1988, 31, 318-322, Alexander, J. et al). Other conventional procedures for the selection and preparation of suitable prodrugs are known in the art and are described, for example, in WO 00/23419; *Design of Prodrugs*, H. Bundgaard, Ed., Elsevier Science Publishers, 1985; *Methods in Enzymology*, 42: 309-396, K. Widder, Ed, Academic Press, 1985; *A Textbook of Drug Design and Development*, Krogsgaard-Larsen and H. Bundgaard, Eds, Chapter 5, p 113-191 (1991); *Advanced Drug Delivery Reviews*, 8; 1-38 (1992); *Journal of Pharmaceutical Sciences*, 77;285 (1988), H. Bundgaard, et al; *Chem Pharm Bull*, 32692 (1984), N. Kakeya et al and *The Organic Chemistry of Drug Desig and Drug Action*, Chapter 8, pp 352-401, Academic press, Inc., 1992.

Suitable pharmaceutically acceptable salts of compounds of formula (I) include, but are not limited to salts of pharmaceutically acceptable inorganic acids such as hydrochloric, sulphuric, phosphoric nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicyclic sulphanilic, aspartic, glutamic, edetic, stearic, palmitic, oleic, lauric, pantothenic, tannic, ascorbic, fendizoic, 4-4'-methylenebis-3-hydroxy-2-naphthoic acid, o-(p-hydroxybenzoyl) benzoic, 4'-4"-dihydroxytriphenylmethane-2-carboxylic acid and valeric acids. Base salts include, but are not limited to, those formed with pharmaceutically acceptable cations, such as sodium, potassium, lithium, calcium, magnesium, ammonium and alkylammonium. Basic nitrogen-containing groups may be quaternised with such agents as lower alkyl halide, such as methyl, ethyl, propyl, and butyl chlorides, bromides and iodides or dialkyl sulfates such as dimethyl and diethyl sulfate.

The compounds of the invention may be in crystalline form either as the free compounds or as solvates and it is intended that both forms are within the scope of the present invention. The term "solvate" refers to a complex or aggregate formed by one or more molecules of a solute, i.e. compounds contemplated by the invention, and one or more molecules of a solvent. Suitable solvents are well understood in the art and include for example, of water, i.e. to form hydrates, and common organic solvents such as alcohols (methanol, ethanol, isopropanol) and acetic acid. Methods of solvation are generally known within the art, for example, recrystallization from an appropriate solvent.

Tautomeric forms of compounds described herein, such as keto-enol tautomers, are also contemplated to be part of the invention where appropriate.

It will also be recognised that certain compounds of formula (I) may possess asymmetric centres and are therefore capable of existing in more than one stereoisomeric form, such as enantiomers and diastereomers. The invention thus also relates to optically active compounds and compounds in substantially pure isomeric form at one or more asymmetric centres, e.g., diastereoisomers and enantiomers having greater than about 90% ee, such as about 95% or 97% ee or greater than 99% ee, as well as mixtures, including racemic mixtures, thereof. Such isomers may be prepared by asymmetric synthesis, for example using chiral intermediates, enzymes, or mixtures may be resolved by conventional methods, e.g., chromatography, recrystallization, or use of a resolving agent.

The compounds of the invention may also be used to treat non-human subjects and may therefore be presented as veterinary compositions. These may be prepared by any suitable means known in the art. Examples of such compositions include those adapted for:

(a) oral administration, external application (e.g. drenches including aqueous and non-aqueous solutions or suspensions), tablets, boluses, powders, granules, pellets for admixture with feedstuffs, pastes for application to the tongue;

(b) parenteral administration, e.g. subcutaneous, intramuscular, intravenous or intracerebroventricular injection as a sterile solution or suspension;

(c) topical application e.g. creams, ointments, gels, lotions etc.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

The following examples are provided for the purpose of illustrating certain embodiments of the invention and are not intended to limit the generalities hereinbefore described.

EXAMPLES

Example 1

Four compounds (1-4) were prepared and tested for IRAP inhibitory activity and compared against the most potent exemplified compound of WO 2006/026832.

Preparation of Comparative Compound 1 from WO 2006/026832

(i) 3-Pyridine carboxaldehyde (2.2 g) and ethylcyanoacetate (2.3 g) were heated at reflux in toluene together with acetic acid (100 µl) and piperidine (40 µl). Nitrogen was blown over the surface to help remove water. A precipitate formed on cooling and standing, with the addition of pet. spirit. A cream-coloured crystalline solid (3.0 g) was collected.

(ii) (Reference: *Org. Prep and Proc.*, 1999, 31, 305)

The ethylacrylate ester product of (i) above (1.0 g) was dissolved, together with resorcinol (0.55 g) in 15 ml ethanol at 80° C. Piperidine (5 drops) was added to the solution and the mixture heated at reflux for 4 hours. A white solid was collected and the title compound separated from the dimeric product to afford 40 mg of the desired compound.

The desired product was obtained in 48% yield, free of dimeric product when 1.5 equivalents of resorcinol was used on a 4.9 mmol scale.

Compound 1

Ethyl 2-amino-7-hydroxy-4-quinolin-4-yl-4H-chromene-3-carboxylate (i) Ethyl 2-cyano-3-quinolinyl-4-ylacrylate was obtained in a similar manner to that described above by reaction of 4-quinolinecarboxaldehyde and ethyl cyanoacetate. The product precipitated from the reaction mixture and was isolated by filtration (1.432 g, 61%).

(ii)

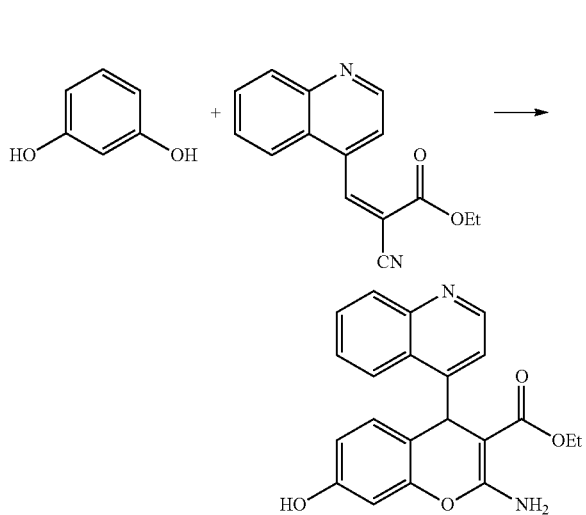

A mixture of resorcinol (126 mg, 1.14 mmol) and ethyl 2-cyano-3-quinolin-4-ylacrylate (254 mg, 1.01 mmol) was suspended in absolute ethanol (3.0 mL). Piperidine (20 µL) was added and the mixture heated at reflux for 3 h. A precipitate formed on cooling. The mixture was filtered. The residue was dissolved in a mixture of ethyl acetate (20 mL) and ethanol (5 mL). Silica gel 60 (0.9 g) was added and the mixture evaporated to dryness. Purified by flash chromatography over silica gel 60, 40-63 µm (eluent: 75% ethyl acetate/petroleum spirits (8×20 mL fractions), packing height: 18 cm, column diameter: 1 cm). The fractions containing the major band ($R_f$ 0.43, eluent: 75% ethyl acetate/petroleum spirits, fractions 3-5) were combined and evaporated to dryness. The residue was dried in a vacuum oven (80° C., 200 mbar) for 6 h to give the title compound (115 mg, 32%) as a yellow powder.

HPLC (214 nm) $t_R$=6.02 min (97%).

$^1$H NMR (400 MHz, DMSO-d$_6$) δ 0.61 (t, J=7.2 Hz, 3H), 3.64-3.79 (m, 2H), 5.78 (s, 1H), 6.37 (dd, J=8.4, 2.4 Hz, 1H), 6.48 (d, J=2.4 Hz, 1H), 6.82 (d, J=8.4 Hz, 1H), 7.19 (d, J=4.4 Hz, 1H), 7.64-7.80 (m, 4H), 8.00 (dd, J=8.4, 1.2 Hz, 1H), 8.64 (br d, J=8.4 Hz, 1H), 8.74 (d, J=4.8 Hz, 1H), 9.67 (s, 1H).

Compound 2

Ethyl 2-(acetylamino)-7-hydroxy-4-pyridin-3-yl-4H-chromene-3-carboxylate

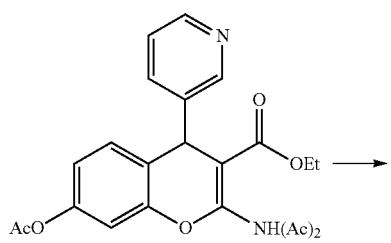

-continued

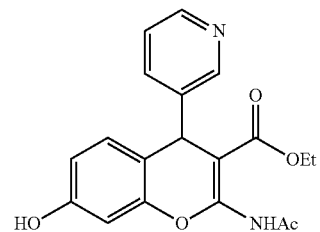

Ethyl 7-(acetyloxy)-2-(diacetylamino)-4-pyridin-3-yl-4H-chromene-3-carboxylate (6.989 g, 15.9 mmol) was dissolved in absolute ethanol (50 mL). Hydrazine hydrate (950 µL, 19.5 mmol) was added and the mixture stirred at room temperature for 6 h. The reaction mixture was evaporated to dryness to give an orange solid. The residue was dissolved in a mixture of ethyl acetate (200 mL) and ethanol (50 mL). Silica gel 60 (35 g) was added and the mixture evaporated to dryness. Purified by flash chromatography over silica gel 60, 40-63 µm (eluent: 75% ethyl acetate/petroleum spirits (54× 100 mL fractions), packing height: 15 cm, column diameter: 5 cm). The fractions containing the major band ($R_f$ 0.26, eluent: 75% ethyl acetate/petroleum spirits, fractions 15-53) were combined and evaporated to dryness to give the title compound (3.307 g, 59% yield) as a pale yellow powder.

HPLC (214 nm) $t_R$=5.05 min (99%).

$^1$H NMR (400 MHz, DMSO-d$_6$) δ 1.09 (t, J=7.0 Hz, 3H), 2.08 (s, 3H), 3.99 (q, J=6.9 Hz, 2H), 4.99 (s, 1H), 6.47 (d, J=2.4 Hz, 1H), 6.55 (dd, J=8.4, 2.4 Hz, 1H), 7.10 (d, J=8.4 Hz, 1H), 7.27 (dd, J=7.8, 4.6 Hz, 1H), 7.57-7.62 (m, 1H), 8.36 (dd, J=4.8, 1.6 Hz, 1H), 8.54 (d, J=2.0 Hz, 1H), 9.75 (br s, 1H), 10.35 (br s, 1H).

LC/MS $t_R$=5.43 min (355.5 [M+H]$^+$).

MP 216-218° C.

Compound 3

Ethyl 2-amino-7-hydroxy-4-quinolin-3-yl-4H-chromene-3-carboxylate (i) Ethyl 2-cyano-3-quinolin-3-ylacrylate was obtained in a similar manner to that described above by reaction of 3-quinolinecarboxaldehyde and ethyl cyanoacetate. The product precipitated from the reaction mixture and was isolated by filtration (1.023 g, 92%).

(ii)

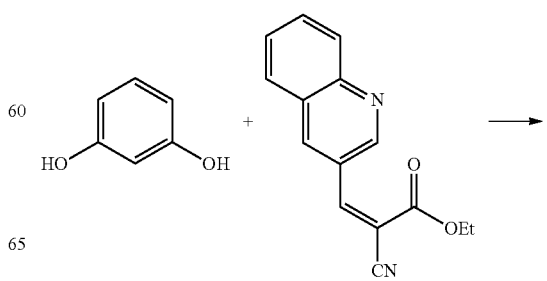

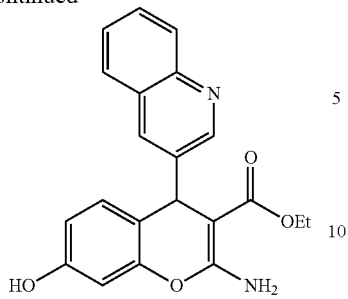

A mixture of resorcinol (512 mg, 4.65 mmol), ethyl 2-cyano-3-quinolin-3-ylacrylate (1.003 g, 3.98 mmol), piperidine (80 μL, 0.81 mmol) and absolute ethanol (12 mL) was heated at reflux for 3 h. A precipitate formed on cooling. Water (36 mL) was added and the mixture filtered. The residue was washed with water (2×30 mL), dried in a vacuum desiccator over silica gel, washed with ethyl acetate (5 mL) and dried under high vacuum (180° C., 0.5 mbar) for 90 min to give an orange powder (794 mg, 55% yield). A portion of this product (596 mg) was suspended in ethanol (20 mL). Silica gel 60 (3.1 g) was added and the mixture evaporated to dryness. Purified by flash chromatography over silica gel 60, 40-63 μm (eluent: 75% ethyl acetate/petroleum spirits (19×40 mL fractions), ethyl acetate (16×40 mL fractions), ethanol (7×40 mL fractions), packing height: 15 cm, column diameter: 2.5 cm). The pale yellow fractions containing the major band ($R_f$ 0.33, eluent: 75% ethyl acetate/petroleum spirits, fractions 4-37) were combined and evaporated to dryness. The residue was dried under high vacuum (150° C., 0.75 mbar) for 15 min to give the title compound (282 mg, 47% recovery) as a yellow powder.

HPLC (214 nm) $t_R$=5.86 min (92%).

$^1$H NMR (400 MHz, DMSO-$d_6$) δ 1.00 (t, J=7.0 Hz, 3H), 3.92 (q, J=7.1 Hz, 2H), 5.05 (s, 1H), 6.45-6.52 (m, 2H), 7.02 (d, J=8.8 Hz, 1H), 7.54 (t, J=7.4 Hz, 1H), 7.63-7.78 (m, 3H), 7.93 (t, J=8.4 Hz, 2H), 7.98 (d, J=2.0 Hz, 1H), 8.75 (d, J=2.0 Hz, 1H), 9.70 (s, 1H).

LC/MS $t_R$=6.25 (363.4 [M+H]$^+$) min.

MP 229-231° C.

Compound 4

Ethyl 2-(acetylamino)-7-hydroxy-4-quinolin-3-yl-4H-chromene-3-carboxylate

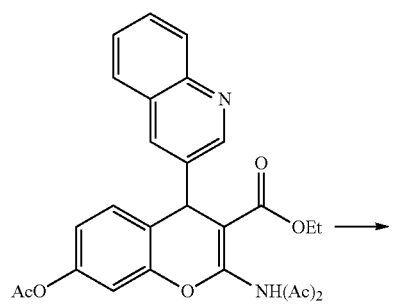

Ethyl 7-(acetyloxy)-2-(diacetylamino)-4-quinolin-3-yl-4H-chromene-3-carboxylate (268 mg, 0.55 mmol) was dissolved in absolute ethanol (1.7 mL). Hydrazine hydrate (35 μL, 0.72 mmol) was added and the mixture stirred at room temperature for 1 h. The reaction mixture was evaporated to dryness. $^1$H NMR analysis showed incomplete conversion of the starting material. The product was suspended in absolute ethanol (1.7 mL) and hydrazine hydrate (35 μL, 0.72 mmol) added. The mixture was stirred at room temperature for 2 h. The mixture was filtered. The residue was washed with ethanol (1.0 mL) and ethyl acetate (2.0 mL). The residue was dissolved in boiling ethanol (16 mL) and the volume reduced to half by heating under a stream of nitrogen. The mixture was cooled to 4° C. and filtered. The residue was dried at the pump to give the title compound (65 mg, 29% yield) as pale yellow needles.

HPLC (214 nm) $t_R$=5.84 min (98.5%).

NMR (400 MHz, DMSO-$d_6$) δ 1.07 (t, J=7.2 Hz, 3H), 2.11 (s, 3H), 3.98 (q, J=7.1 Hz, 2H), 5.20 (s, 1H), 6.51 (d, J=2.0 Hz, 1H), 6.55 (dd, J=8.4, 2.4 Hz, 1H), 7.16 (d, J=8.4 Hz, 1H), 7.57 (t, J=7.4 Hz, 1H), 7.69 (t, J=7.6 Hz, 1H), 7.89 (d, J=8.0 Hz, 1H), 7.96 (d, J=8.0 Hz, 1H), 8.13 (d, J=2.0 Hz, 1H), 8.89 (d, J=2.0 Hz, 1H), 9.78 (br s, 1H), 10.41 (br s, 1H).

LC/MS $t_R$=6.27 min (405.4 [M+H]$^+$).

MP 248-251° C.

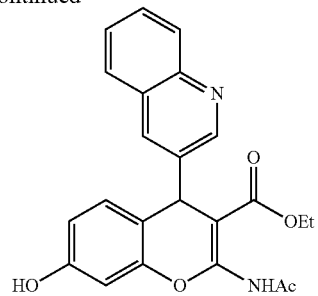

Example 2

An in vitro enzymatic assay was used to initially assess IRAP inhibitory activity.

IRAP Enzymatic Assay

Crude membranes were prepared from HEK 293T cells transfected with IRAP or empty vector, then solubilized in buffer consisting of 50 mM Tris-HCl, 1% Triton X-100, pH 7.4 at 4° C. under agitation over 5 h. After solubilization, the membranes were pelleted by centrifugation at 23,100 g for 15 min at 4° C., and the supernatant was reserved as the source of IRAP activity. The enzymatic activities of MAP were determined by the hydrolysis of the synthetic substrate Leu-MCA (Sigma-Aldrich, Missouri, USA) monitored by the release of a fluorogenic product, MCA, at excitation and emission wavelengths of 380 and 440 nm, respectively. Assays were performed in 96-well plates; each well contains between 0.2-10 μg solubilized membrane protein, a range of concentration of substrate in a final volume of 100 μL 50 mM Tris-HCl buffer (pH 7.4). Non-specific hydrolysis of the substrate was corrected by subtracting the emission from incubations with membranes transfected with empty vector. Reactions proceeded at 37° C. for 30 min within a thermostatted FLEX station fluorescence microplate reader (Molecular Devices, Sunnyvale, Calif.). The kinetic parameters ($K_m$ and V) were determined by non-linear fitting of the Michaelis-Menten equation (GraphPad Prism, GraphPad Software Inc., CA, USA); final concentrations of Leu-MCA of 15.6 μM-1 mM. Inhibitor constants ($K_i$) for the competitive inhibitors were calculated from the relationship $IC_{50}=K_i(1+[S]/K_m)$, where $IC_{50}$ values were determined over a range of inhibitor concentrations ($10^{-9}$ to $10^{-4}$ M). $K_m$ values of IRAP for Leu-MCA were determined from the kinetic studies. Binding affinities of the compounds to IRAP were examined by monitoring the inhibition of the hydrolysis of Leu-MCA in the presence of increasing concentrations of the compounds ($10^{-8}$ to $10^{-3}$ M). All data obtained were from at least three separate experiments performed in duplicate.

The results are depicted in Table 2-1.

| Compounds | $K_i$ (uM) | $IC_{50}$ | Structures |
|---|---|---|---|
| 1 | 0.9 | 1.5 μM | (quinolin-4-yl chromene structure with OEt, OH, NH₂) |
| 2 | 0.48 | 0.79 μM | (pyridin-3-yl chromene structure with OEt, OH, NHAc) |
| 3 | 0.36 | 0.6 μM | (quinolin-3-yl chromene structure with OEt, OH, NH₂) |
| 4 | 0.02 | 40 nM | (quinolin-3-yl chromene structure with OEt, OH, NHAc) |
| Compound 1 from WO 2006/026832 (Comparative) | 2.0 | 3 μM | (pyridin-3-yl chromene structure with ethyl ester, OH, NH₂) |

In order to see whether the compounds are selective or specific for IRAP, the inhibitory activities of Compounds 2-4 for other zinc-dependent metallopeptidases were determined in 96-well microtiter plates with absorbance monitored on a Wallac Victor 3 spectrophotometer.

Glucose-6-phosphate dehydrogenase and hexokinase activity. Glucose-6-phosphate dehydrogenase and hexokinase activity in the absence and presence of the compounds was determined in a fluorimetric assay. Ten mM Tris $MgCl_2$ buffer (total volume of 200 ml) containing glucose-6-phosphate dehydrogenase, 0.3 M ATP, 30 mM NADP+ was added to 96 well microtitre plate together with 20 µl of compound, a reading at excitation 350 nm and emission 510 nm was taken followed by the addition of hexokinase and another reading.

Leukotriene A4 hydrolase assay. Recombinant human LTA4H (Cayman Chemicals Michigan USA) (1-20 µg) was incubated at room temperature with alanine-p-nitroanilide as substrate in 50 mM Tris-HCl buffer, pH 8.0, containing 100 mM KCl with or without increasing concentrations of an inhibitor. The absorbance at 405 nm was measured at 10 min intervals.

Aminopeptidase N assay. 5 mU of aminopeptidase M (Sigma Aldrich) was incubated with 100 µM of substrate alanine-β-naphthylamide (Sigma Aldrich) in Tris buffered saline (50 mM Tris-HCl, 150 mM NaCl pH 7.5) at 25° C. IRAP inhibitors (1-10 µM) were added after 1 minute and fluorescence at 405 nm was followed.

Angiotensin converting enzyme assay. The enzyme (final concentration 0.02 pmol/100 µL) was incubated with 200 µL of assay solution that included 5 mmol/L HHL in 100 mmol/L potassium buffer (pH 8.3) that contained 300 mmol/L NaCl and $10^{-4}$ mol/L $ZnSO_4$ for 3 hours at 37° C. The enzymatic reaction was stopped by the addition of 1.5 mL of 0.28N NaOH, 100 µL of o-phthaldialdehyde (20 mg/mL) in methanol was added and the fluorescent reaction stopped by the addition of 200 µL of 3N HCl. The product, L-His-Leu, was measured fluorometrically (360 nm excitation and 500 nm emission).

Limited inhibition of control enzymes was observed. The results are depicted in Table 2-2 and are expressed as % inhibition of the catalytic activity of the enzyme at the given concentration.

TABLE 2-2

| | Compound 2 | | Compound 3 | | Compound 4 | |
| --- | --- | --- | --- | --- | --- | --- |
| | 100 µM | 10 µM | 100 µM | 10 µM | 100 µM | 10 µM |
| Glucose-6-phosphate dehydrogenase/glucose hexokinase | 0 | ND* | 0 | ND | 0 | ND |
| Leukotriene A4 hydrolase | 0 | ND | 4 | ND | 25 | 0 |
| Aminopeptidase N | ND | 13 | ND | 12 | 14 | 3 |
| Angiotensin converting enzyme 1 | 3 | 9 | 3 | 0 | 0 | 0 |

*ND = not determined

Example 3

The effects of Compound 2 on performance in different memory tasks in vivo were investigated.

Surgical Preparation of Rats

All experiments were performed according to the National Health and Medical Research Council of Australia "Code of practice for the care and use of animals for scientific purposes". Male Sprague Dawley rats, (250-270 g) are housed individually and given water and standard rat chow ad libitum. On the day of surgery, the rats were anaesthetized with 5% isofluorane, placed in a stereotaxic frame and maintained on 2% isofluorane for the duration of the cannula implantation procedure. The rats were stereotaxically implanted with chronic indwelling cannula (Plastics One) into the cerebral lateral ventricles using the following flat skull coordinates 0.8 mm posterior to Bregma, 1.55 mm lateral to midline and 3.5 mm ventral to the dura. The cannula was then secured to the skull with stainless steel screws and dental cement. Seven days following surgery, proper cannula placement was verified by a bolus injection of angiotensin II (1 nmol/µl). Lack of a robust dipsogenic response within 5 min of angiotensin II administration would suggest misplacement of the cannula and the animal was then excluded from further studies.

Novel Object Recognition Task (Bevins et al, 2006)

The rats are allowed at least 5 days post-operative recovery prior to use in any behavioural paradigms. On the day of the acquisition trial, the rats were habituated for 5 min in the testing box (made from grey perspex of dimensions 60 cm width×60 cm length×50 cm height) in diffuse dim light and then returned to their home cage. The animals were then rested for at least 2 h and then injected with 1 nmol or 0.1 nmol Compound 2 in 2 µl of 10% dimethyl sulfoxide (DMSO). Control animals received 2 µl of 10% DMSO. Following drug administration, the rats were returned to their home cage for 5 min and then placed in the testing box facing the opposite direction to 2 identical objects that have been secured to the floor in adjacent corners of the box. The rats were allowed 5 min to explore the objects and the definition of explore is that the animal's nose is less than 2 cm from object when it is facing the object. Animals that displayed a lack of interest in the object, exploration time of less than 15 secs were excluded from the study at this stage. The animals were then returned to their home cage during the intertrial interval of 20 h. On day 2 of testing, one of the objects were replaced by a novel object made from the same material but of a different shape—the rats were given 2 mins in the box. The recognition index was determined as the time spent exploring the novel object minus the time spent on the familiar object divided by the time spent on both object.

Spontaneous Alternation Plus Maze (McNay et al, 2000)

The plus maze was composed of four arms with each arm measuring 75×10×20 cm. The floor and walls of the central platform and the floors of the arms were made of black plastic. Spontaneous alternation testing was conducted by placing the rat on the center platform of the maze and allowing 20 min of unimpeded exploration. The number and sequence of arm entries were recorded for calculation of a percent alternation score. An alternation consisted of 4 different arm choices of 5 consecutive arm entries. A 4/5 alternation score was computed by dividing the number of observed alternations in overlapping quintuplets by the number of possible alternations and multiplying the quotient by 100.

Elevated Plus Maze

The elevated plus maze was used to investigate the potential effect of IRAP inhibitors on stress or anxiety. The elevated plus maze consists of two open arms (70×10 cm) with a 5 cm high surrounding wall and two enclosed arms (70×10 cm) with a 27 cm high surrounding wall. The floor of the open and closed arms are white laminate, the open arm walls are clear perspex, and the closed arms walls dark grey perspex. The maze is elevated 85 cm above the ground in the centre of a room that is lit by overhead lights generating 124 lux. Naive rats, treated either with 1 nmol Compound 2 dissolved in 10% DMSO or vehicle, were placed 5 min after the icy injection, on the central platform facing one of the closed arms and behaviour monitored for 10 min. The time spent in the closed arms compared to the open arms was a measure of the anxiety status of the animals.

Locomotor Cell Activity

Locomotor activity of rats treated with 1 nmol Compound 2 intracerebrocentricularly was monitored in special cages measuring 40×40×40 cm (Coulbourn Instruments, Philadelphia, USA) equipped with harmless infrared photobeams. Activity was measured when pairs of photobeams spaced 2.54 cm apart providing a 1.27 cm spatial resolution were crossed. Data was collected and analysed using TruScan Photo Beam Activity system (Coulbourn Instruments, Philadelphia, USA). Each rat was placed in the arena for 30 min.

The results are depicted in Tables 3-A1-3-A2 and 3-B1-3-B3.

Rats treated with Compound 2, at 1 and 0.1 nmole intracerebroventricularly, exhibited better recognition of a novel object after 24 h compared to vehicle treated control rats, n=10/group and *p<0.05 (Table 3-A1). Rats treated with 0.1 nmole exhibited significantly enhanced spontaneous alternation scores compared to vehicle treated control rats, n=8/group and **p<0.01 (Table 3-A2). Rats treated with Compound 2 at 0.1 and 1 nmol intracerebroventricularly, were not significantly more or less stressed than vehicle treated control rats as determined by time spent in the open arm of the elevated plus maze. n=8 per group (Table 3-B1). Rats treated with Compound 2 at 0.1 and 1 nmol intracerebroventricularly, did not exhibit increased or decreased locomotor activity compared to vehicle treated rats as determined by crossing of infrared beams and total distance travelled in a locomotor cell over a period of 30 mins. n=8 per group (Table 3-B2).

TABLE 3-A1

| Treatment | Recognition Index |
|---|---|
| Vehicle | 5.04 ± 5.43 |
| 0.1 nmol | 35.82 ± 7.30* |
| 1 nmol | 45.09 ± 9.97* |

TABLE 3-A2

| Treatment | Spontaneous Alternation Score (%) |
|---|---|
| Vehicle | 62.07 ± 1.55 |
| 0.1 nmol | 73.70 ± 3.14** |
| 1 nmol | 64.34 ± 2.49 |

TABLE 3-B1

| Treatment | Time spent in the open arm (% control) |
|---|---|
| Vehicle | 100 ± 31.26 |
| 0.1 nmol | 121.62 ± 28.26 |
| 1 nmol | 127.88 ± 19.18 |

TABLE 3-B2

| Treatment | Distance travelled (% control) |
|---|---|
| Vehicle | 100 ± 3 |
| 0.1 nmol | 85.12 ± 12.99 |
| 1 nmol | 90.16 ± 6.73 |

Example 4

Hippocampal glucose uptake assay. Eight week old male Sprague-Dawley rats were deeply anaesthetised with Isofluorothane and killed by decapitation. The brains were rapidly removed and placed into ice-cold, 95% $O_2$, 5% $CO_2$-bubbled artificial cerebrospinal fluid (aCSF: 124 mM NaCl, 2.5 mM KCl, 2 mM $CaCl_2$, 2 mM $MgSO_4$, 26 mM $NaHCO_3$, 1.25 mM $NaH_2PO_4$ pH 7.4) supplemented with 10 mM D-glucose (Sigma). Under aCSF, the hippocampal hemispheres were rapidly dissected out and 200 µm slices prepared on McIlwain tissue chopper with an ice-cold blade and stage. Slices from each hemisphere were kept together and transferred to freshly 95% $O_2$, 5% $CO_2$-bubbled aCSF supplemented with 10 mM D-glucose at 37° C. for 1 hour. All subsequent steps were carried out at 37° C. in a gently shaking chamber with continuous infusion of 95% $O_2$, 5% $CO_2$. Slices from one hemisphere were used as a basal control while slices from the other hemisphere were stimulated, providing an internal control for each animal. Hemisphere pairs were transferred to 95% $O_2$, 5% $CO_2$ bubbled aCSF supplemented with 0.1 mM D-glucose and 2 mM 2-deoxyglucose and 1 mM dbcAMP for 15 min following which slices from one hemisphere were stimulated by the addition of 100 nM HFI419 while the other hemisphere provided an internal control for each animal and 0.1 µCi 2-Deoxy-d-[2,6-$^3$H]glucose ($^3$H-2DG) (specific activity 49 Ci/mmol; Amersham Biosciences, NSW, Australia) was added to a final concentration of 0.1 µM in both basal and stimulated hemispheres for five minutes. Following uptake, hemispheres were rapidly rinsed in four changes of ice cold PBS and slices transferred to pre-weighed filter paper and allowed to dry. Dried slices from each hemisphere were weighed and solubilized overnight with Soluene-350 (Perkin Elmer, MO, USA). Tritium content was measured in a Liquid Scintillation Analyser 1900TR (Perkin Elmer, MA, USA).

An increase in dibutyryl cAMP-evoked glucose uptake in response to Compound 2 was observed.

The results are depicted in Table 4-1.

The effect of Compound 2 was tested in vitro on the metabolic demands of neurones.

TABLE 4-1

| | Fold change in 3H-2DOG uptake |
|---|---|
| dbcAMP | 1 |
| dbcAMP & Compound 2 | 1.7 |

BIBLIOGRAPHY

Albiston et al., *J Biol Chem* 276: 48263-48266, 2001.
Albiston et al., *Behav Brain Res* 154: 239-243, 2004.
Bevins et al., *Nat Protoc* 1(3): 1306-11, 2006.
Braszko, et al., *Neuroscience* 27: 777-783, 1988.
Dash et al., *J. Neurosci.* 26: 8048-56, 2006.
Fernando et al., *Journal of Comparative Neurology* 487: 372-390, 2005.
Greferath et al., *Neuroscience* 100: 363-373, 2000.
Herbst et al., *Am. J. Physiol.* 272: E600-6, 1997.
Keller et al., *J. Biol Chem* 270: 23612-23618, 1995.
Lee et al., *Neuroscience* 124: 341-349, 2004.
Lew et al., *Journal of Neurochemistry* 86: 344-350, 2003.
McNay et al., *Proc Natl Acad Sci USA,* 97(6): 2881-5, 2000.
Pederson et al., *Regul Pept* 74: 97-103, 1998.
Pederson et al., *Regul Pept* 102: 147-156, 2001.
Rogi et al., *J Biol Chem* 271: 56-61, 1996.
Waters et al., *J Biol Chem* 272: 23323-23327, 1997.
Wright et al., *Brain Res Bull* 32: 497-502, 1993.
Wright et al., *Brain Res* 717: 1-11, 1996.
Wright et al., *J Neurosci* 19: 3952-3961, 1999.
Zhang et al., *J Pharmacol Exp Ther* 289: 1075-1083, 1999.

The invention claimed is:
1. A compound of Formula (I)

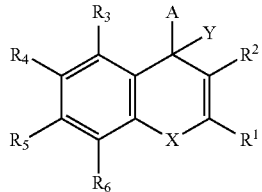

wherein:
A is pyridyl which may be optionally substituted;
$R^1$ is $NHCOR^8$;
X is O;
$R^8$ is selected from hydrogen, optionally substituted alkyl and optionally substituted aryl;
$R^2$ is CN, $CO_2R^9$, $C(O)O(O)R^9$, $C(O)R^9$ or $C(O)NR^9R^{10}$ wherein $R^9$ and $R^{10}$ are independently selected from alkyl, alkenyl, alkynyl, aryl, heteroaryl, carbocyclyl, heterocyclyl, each of which may be optionally substituted, and hydrogen; or $R^9$ and $R^{10}$, together with the nitrogen atom to which they are attached, form a 3-8-membered ring which may be optionally substituted;
$R^3$-$R^6$ are independently selected from hydrogen, halo, nitro, cyano alkyl, alkenyl, alkynyl, aryl, heteroaryl, heterocyclyl, carbocyclyl, hydroxy, alkoxy, alkenyloxy, alkynyloxy, alkynyloxy, aryloxy, heteroaryloxy, heterocyclyloxy, amino, acyl, acyloxy, carboxy, carboxyester, methylenedioxy, amido, thio, alkylthio, alkenylthio, alkynylthio, arylthio, heteroarylthio, heterocyclylthio, carbocyclylthio, acylthio and azido, each of which may be optionally substituted where appropriate, or any two adjacent $R^3$-$R^6$, together with the atoms to which they are attached, form a 3-8-membered ring which may be optionally substituted; and
Y is hydrogen or $C_{1-10}$alkyl,
or a pharmaceutically acceptable salt thereof.

2. A compound according to claim 1 wherein $R^1$ is $NHCOC_{1-6}$alkyl, NHCOphenyl or NHCObenzyl.

3. The compound of claim 1, wherein the compound is
Ethyl 2-(acetylamino)-7-hydroxy-4-pyridin-3-yl-4H-chromene-3-carboxylate
or a pharmaceutically acceptable salt thereof.

4. A composition comprising a compound according to claim 1 together with a pharmaceutically acceptable carrier or excipient.

5. The compound of claim 1, wherein $R^2$ is $CO_2R^9$ and $R^3$-$R^6$ are selected from hydrogen, hydroxy, acyl, acyloxy, carboxy and carboxyester.

* * * * *